(12) United States Patent
Liu et al.

(10) Patent No.: US 9,580,470 B2
(45) Date of Patent: Feb. 28, 2017

(54) HIGH-PURITY CYCLOPEPTIDE CRYSTAL AS WELL AS PREPARATION METHOD AND USE THEREOF

(71) Applicant: SHANGHAI TECHWELL BIOPHARMACEUTICAL CO., LTD., Shanghai (CN)

(72) Inventors: Shidong Liu, Shanghai (CN); Zhaoli Zhang, Shanghai (CN); Xiusheng Wang, Shanghai (CN); Xiao Zhang, Shanghai (CN); Zhijun Tang, Shanghai (CN); Xiaoming Ji, Shanghai (CN)

(73) Assignee: Shanghai Techwell Biopharmaceutical Co., LTD., Shanghai (CN)

( * ) Notice: Subject to any disclaimer, the term of this patent is extended or adjusted under 35 U.S.C. 154(b) by 35 days.

(21) Appl. No.: 14/389,352

(22) PCT Filed: Mar. 29, 2013

(86) PCT No.: PCT/CN2013/073512
§ 371 (c)(1),
(2) Date: Sep. 29, 2014

(87) PCT Pub. No.: WO2013/143499
PCT Pub. Date: Oct. 3, 2013

(65) Prior Publication Data
US 2015/0105331 A1 Apr. 16, 2015

(30) Foreign Application Priority Data
Mar. 30, 2012 (CN) .......................... 2012 1 0090352

(51) Int. Cl.
*A61K 38/12* (2006.01)
*C07K 7/56* (2006.01)
*A61K 38/00* (2006.01)

(52) U.S. Cl.
CPC .............. *C07K 7/56* (2013.01); *A61K 38/00* (2013.01)

(58) Field of Classification Search
None
See application file for complete search history.

(56) References Cited

U.S. PATENT DOCUMENTS 5,376,634 A * 12/1994 Iwamoto et al. ............. 514/3.3

FOREIGN PATENT DOCUMENTS

| CN | 1051757 A | 5/1991 |
| CN | 1059729 A | 3/1992 |
| CN | 1168675 A | 12/1997 |
| WO | WO 2004/014879 | 2/2004 |
| WO | WO 2012/047762 | 4/2012 |

OTHER PUBLICATIONS

PCT International Search Report and Written Opinion dated Jul. 11, 2013 issued in PCT/CN2013/073512 (WO/2013/143499).

* cited by examiner

*Primary Examiner* — James H Alstrum Acevedo
*Assistant Examiner* — Sergio Coffa
(74) *Attorney, Agent, or Firm* — Tom Hunter; Weaver Austin Villeneuve & Sampson LLP

(57) ABSTRACT

A high purity cyclopeptide crystal has a structure shown by Formula I. R represents H or a cation forming a pharmaceutically acceptable salt. Also disclosed are a preparation method and a use of the high-purity cyclopeptide crystal.

9 Claims, 8 Drawing Sheets formula I

HIGH-PURITY CYCLOPEPTIDE CRYSTAL AS WELL AS PREPARATION METHOD AND USE THEREOF

CROSS-REFERENCE TO RELATED APPLICATIONS

This application is a 371 National Phase of PCT/CN2013/073512, filed on Mar. 29, 2013, which claims benefit of and priority to CN 201210090352.1, filed on Mar. 30, 2012, which is incorporated herein by reference in its entirety for all purposes.

TECHNICAL FIELD

The present invention relates to crystals of a compound; and more specifically, relates to crystals of high-purity cyclopeptide substance and preparation method and use thereof.

BACKGROUND

Fungal infection has become the leading cause for high morbidity and mortality in immunodeficient patients. During the past 20 years, the incidence of fungal infection increased significantly. People at high-risk of fungal infections includes critical patients, surgical patients and those patients suffering from HIV infection, leukemia and other tumors. Patients with organ transplant are also at high risk of fungal infection.

Echinocandins, as a new class of antifungal agents, exhibit good effects in the treatment of infections caused by *Candida* or *Aspergillus*. Caspofungin and Micafungin are the representatives of such medicaments. Echinocandins inhibit fungus by suppressing the formation of 1,3-β glycosidic bond, so as to reduce the harm to human body, and reduce the side effects while remaining high efficiency. Therefore, they are safer in use than traditional antifungal agents.

FK463 (sodium Micafungin) is the compound of formula II (R is a sodium ion), which is developed by Japan Fujisawa Toyama Co., Ltd, Takaoka Plant under the trade name Mycamine, and currently sold in several countries as antifungal agent for intravenous administration. It is obtained by cutting the side-chain of FR901379 as precursor (compound of Formula III, R is a sodium ion or a hydrogen ion) by enzyme, thus forming FR179642 (compound of Formula I, R is a hydrogen or a sodium ion) (see U.S. Pat. No. 5,376,634, EP0431350 and Chinese patent CN1161462C for specific methods), and then chemically modifying FR179642 (see Patent Publication WO9611210, WO9857923, WO2004014879 for specific preparation and purification methods).

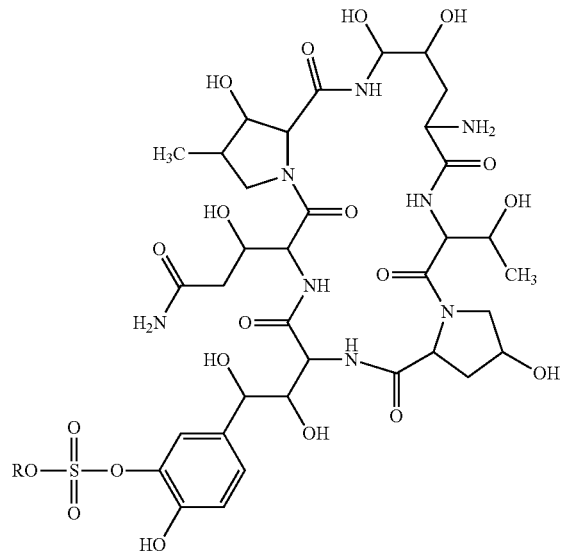

I

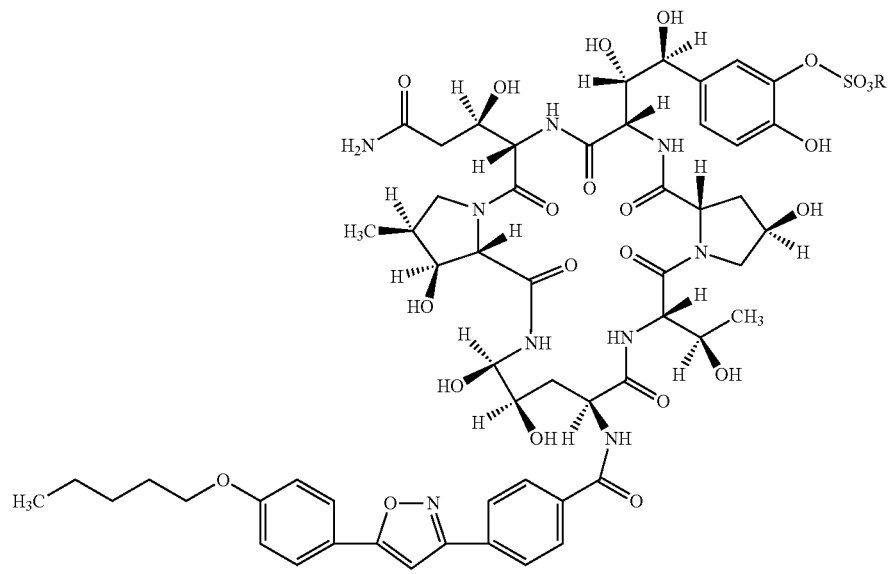
II
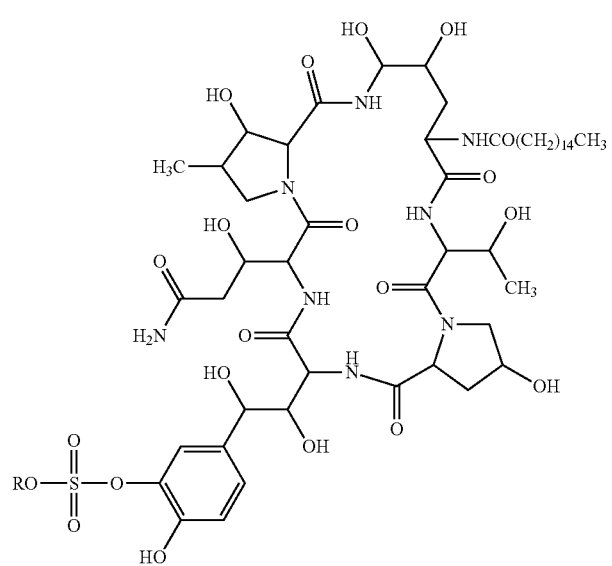
III

Specific scheme is shown as follows:
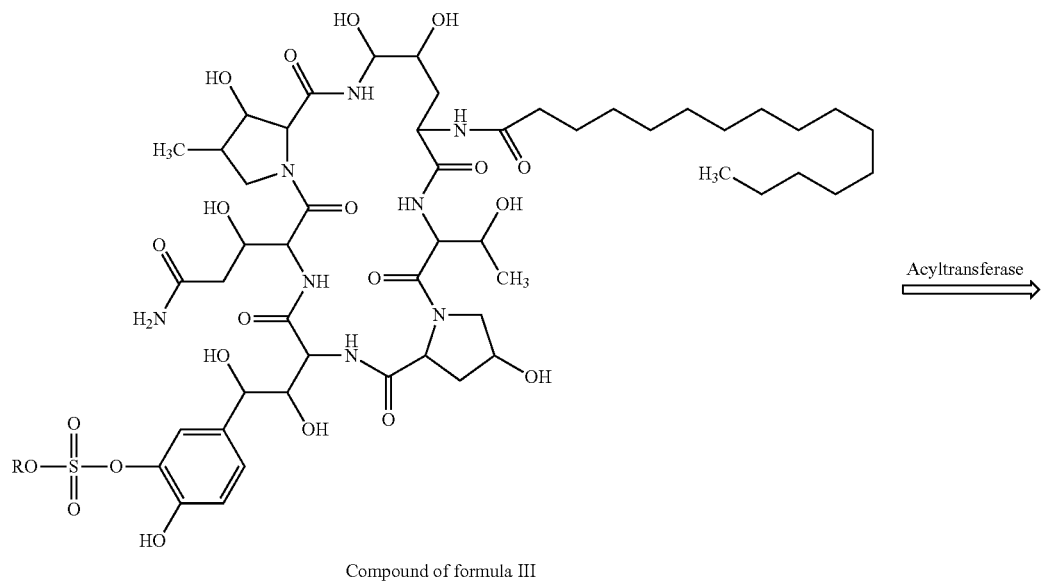
Compound of formula III
Acyltransferase ⇒
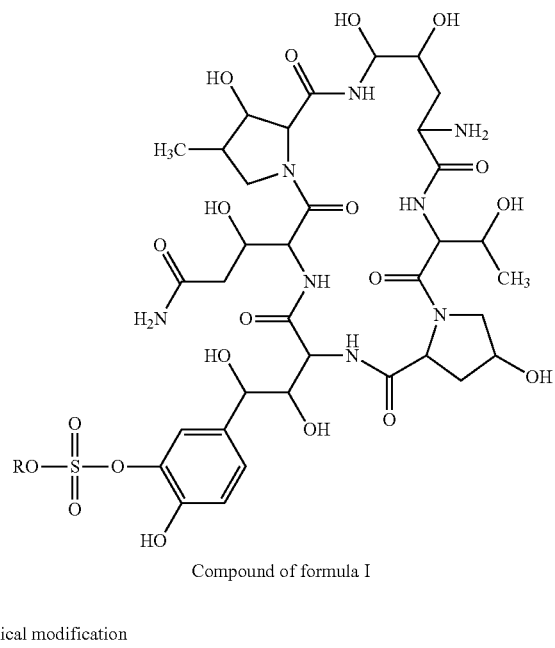
Compound of formula I
⇐ Chemical modification

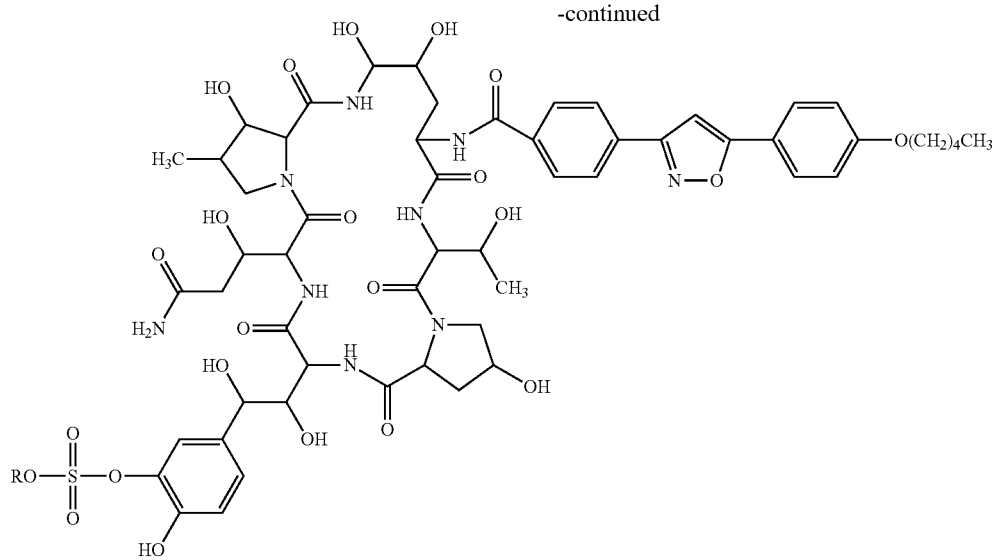

Compound of formula II

As well-known in the art, crystals are generally more stable than the amorphous state. Therefore, the present inventors want to find a suitable crystal of compound of formula I as drug intermediate, so that the compound of formula I is more stable during the storage.

Compound of formula I is difficult to be crystallized, and usually amorphous state. With respect to the final use in the treatment or as an intermediate of compound of formula II, it is desirable to obtain crystals with good stability and high purity.

Several crystals with good stability and suitable for transportation and storage are obtained by the method of the present invention, and the yield during the preparation is high.

SUMMARY OF THE INVENTION

One object of the invention is to provide several crystals of the compound of formula I.

Another object of the invention is to provide the preparation method for giving the novel crystals.

Still another object of the invention is to provide uses of the several crystals.

Preparation of the Crystals of Compound of Formula I

In the present invention, the term "crystal" refers to a solid wherein the molecule or atom complex exhibits a specific arrangement. The present invention provides a method for preparing crystals of the compound of Formula I. For example, crystals with different crystal forms can be prepared by using different solvent systems and drying methods.

After study, the inventors unexpectedly discovered that crystals with excellent morphology can be formed from the compound of formula I by dissolving the compound into water or mixture solution of water-miscible lower alcohols, maintaining the solution comprising the compound of formula I around saturated solubility and controlling pH value of the solution at specified range. The crystal formed from the compound of formula I comprises crystal water. The crystal of compound of formula I will lose crystal water during in-vacuo drying, and crystal transformation will occur. Accordingly, several crystal forms of the compound of formula I before and after crystal transformation as well as the preparation methods thereof are disclosed in the present invention.

In another aspect, when studying solvent systems for the crystal of compound of formula I and the effects of crystal water in a crystal on crystal form, the inventors have discovered that, when lower alcohols and water are used as solvent system for crystallization, crystal forms can be divided into 3 types. Specifically, X-ray powder diffraction (XRPD) patterns for the obtained crystals by using n-propanol, ethanol, isopropanol and water as the crystallization solvent are substantially identical, therefore the crystals can be classified as the same crystal form. Furthermore, another crystal form can be obtained by using methanol and water as the crystallization solvent. Still another crystal form can be obtained by using water as the only crystallization solvent when the temperature is lowered. Upon intensive research on the crystallization solvent, the inventors found that other solvents except the above solvents, such as acetone, acetonitrile, isobutyl alcohol, n-butanol, ethyl acetate, methylene chloride, are not suitable for the crystallization of compound of formula I. The solids obtained by these solvent systems are amorphous solids and possess poor stability.

In another aspect, for the above crystals crystallized in different solvents, the crystal form has a close relationship with the amount of crystal water. The researchers found that crystal transformation will occur during the vacuum-drying of all of the above crystals, that is, during the process of losing water of crystal. For example, crystal A will remain as the same crystal form when the moisture content is at 30%-12%. When the moisture content is reduced to 12%-6% by using vacuum-drying in combination with desiccant ($P_2O_5$) to remove the water from crystal A, crystal A is transformed to crystal B. When the water from crystal B is further removed and the moisture content is reduced to 6%, crystal B is transformed to crystal C. Similarly, crystal D can be obtained by using methanol and water as crystallization solvent system, wherein the moisture content is more than 10%. When the moisture content is reduced to less than 10% by using vacuum-drying in combination with desiccant ($P_2O_5$) to remove the water from crystal D, crystal D is transformed to crystal E. Crystal F can be obtained by using water as the only crystallization solvent, wherein the moisture content is more than 10%. When the moisture content is reduced to less than 10% by using vacuum-drying in combination with desiccant ($P_2O_5$) to remove the water from crystal F, crystal F is transformed to crystal G.

Additionally, during the transformation of crystal A by drying, there may be a state, in which both of crystal A and crystal B are present, and which is called mixed crystal of compound of formula I by the inventors. Similarly, there may be a state, in which both of crystal B and crystal C are present, and which is called mixed crystal of compound of formula I by the inventors. Similarly, there also may be the mixed crystal for crystal D and crystal E, or crystal F and crystal G.

Specific relationships are summarized as follows.

| Crystallization solvent | N-propanol and water | Isopropanol and water | Ethanol and water | Methanol and water | Water |
|---|---|---|---|---|---|
| | Crystal A, moisture content is 30%-12% | | | crystal D, moisture content is not less than 10% | Crystals F, moisture content is not less than 10% |
| Drying to remove water | crystal B, moisture content is 12% to 6% | | | Crystal E, moisture content is less than 10% | Crystal G, moisture content is less than 10% |
| Drying to remove water | Crystal C, moisture content is less than 6% | | | | |

In one aspect, a novel crystalline form of Compound I is provided by the present invention.

Crystal A of a cyclopeptide of formula I, wherein R represents H or a cation capable of forming a pharmaceutically acceptable salt, and X-ray powder diffraction pattern (XRPD) of crystal A shows characteristic peaks at the following 2θ angles: 7.1±0.2, 8.0±0.2, 14.7±0.2, 16.8±0.2, 18.9±0.2, 20.3±0.2, 21.1±0.2.

In another preferred embodiment of the present invention, X-ray powder diffraction pattern (XRPD) of crystal A further shows characteristic peaks at the following 2θ angles: 7.3±0.2, 11.9±0.2, 12.3±0.2, 16.1±0.2, 18.5±0.2, 19.6±0.2, 22.1±0.2, 22.8±0.2, 23.1±0.2, 24.3±0.2, 25.4±0.2, 28.3±0.2, 33.5±0.2.

In another preferred embodiment of the present invention, X-ray powder diffraction pattern (XRPD) of crystal A further shows characteristic peaks at the following 2θ angles: 9.1±0.2, 10.4±0.2, 15.6±0.2, 24.9±0.2, 26.0±0.2, 28.8±0.2.

In another preferred embodiment of the present invention, crystal A has X-ray powder diffraction pattern (XRPD) shown in FIG. 1.

In another preferred embodiment of the present invention, crystal A has IR spectrogram shown in FIG. 2.

Crystal B of a cyclopeptide of formula I, wherein R represents H or a cation capable of forming a pharmaceutically acceptable salt, and X-ray powder diffraction pattern (XRPD) of crystal B shows characteristic peaks at the following 2θ angles: 7.3±0.2°, 11.9±0.2°, 12.8±0.2°, 16.8±0.2°, 19.6±0.2°, 21.1±0.2°, 22.1±0.2°, 22.8±0.2°, 24.3±0.2°, 25.4±0.2°.

In another preferred embodiment of the present invention, X-ray powder diffraction pattern (XRPD) of crystal B further shows characteristic peaks at the following 2θ angles: 8.3±0.2°, 13.4±0.2°, 14.0±0.2°, 15.3±0.2°, 15.9±0.2°, 18.5±0.2°, 26.9±0.2°, 30.5±0.2°.

In another preferred embodiment of the present invention, crystal B has X-ray powder diffraction pattern (XRPD) shown in FIG. 3.

Crystal C of a cyclopeptide of formula I, wherein R represents H or a cation capable of forming a pharmaceutically acceptable salt, and X-ray powder diffraction pattern (XRPD) of crystal C shows characteristic peaks at the following 2θ angles: 8.6±0.2°, 11.9±0.2°.

In another preferred embodiment of the present invention, X-ray powder diffraction pattern (XRPD) of crystal B further shows characteristic peaks at the following 2θ angles: 20.7±0.2°.

In another preferred embodiment of the present invention, crystal C has X-ray powder diffraction pattern (XRPD) shown in FIG. 4.

In another preferred embodiment of the present invention, crystal C has IR spectrogram shown in FIG. 5.

Crystal D of a cyclopeptide of formula I, wherein R represents H or a cation capable of forming a pharmaceutically acceptable salt, and X-ray powder diffraction pattern (XRPD) of crystal D shows characteristic peaks at the following 2θ angles: 5.6±0.2, 14.4±0.2, 19.8±0.2, 22.7±0.2, 23.0±0.2, 23.9±0.2.

In another preferred embodiment of the present invention, X-ray powder diffraction pattern (XRPD) of crystal D further shows characteristic peaks at the following 2θ angles: 7.4±0.2, 8.2±0.2, 9.7±0.2, 12.2±0.2, 16.5±0.2, 18.6±0.2, 22.3±0.2, 28.2±0.2.

In another preferred embodiment of the present invention, X-ray powder diffraction pattern (XRPD) of crystal D further shows characteristic peaks at the following 2θ angles: 6.0±0.2, 6.4±0.2, 6.8±0.2, 11.2±0.2, 14.9±0.2, 15.5±0.2, 17.3±0.2, 19.1±0.2, 20.3±0.2, 21.5±0.2.

In another preferred embodiment of the present invention, crystal D has X-ray powder diffraction pattern (XRPD) shown in FIG. 6.

In another preferred embodiment of the present invention, crystal D has IR spectrogram shown in FIG. 7.

Crystal E of a cyclopeptide of formula I, wherein R represents H or a cation capable of forming a pharmaceutically acceptable salt, and X-ray powder diffraction pattern (XRPD) of crystal E shows characteristic peaks at the following 2θ angles: 9.7±0.2°, 19.8±0.2°, 23.0±0.2°.

In another preferred embodiment of the present invention, X-ray powder diffraction pattern (XRPD) of crystal E further shows characteristic peaks at the following 2θ angles: 6.9±0.2°, 13.0±0.2°, 17.5±0.2°, 24.5±0.2°.

In another preferred embodiment of the present invention, crystal E has X-ray powder diffraction pattern (XRPD) shown in FIG. 8.

In another preferred embodiment of the present invention, crystal E has IR spectrogram shown in FIG. 9.

Crystal F of a cyclopeptide of formula I, wherein R represents H or a cation capable of forming a pharmaceutically acceptable salt, and X-ray powder diffraction pattern (XRPD) of crystal F shows characteristic peaks at the following 2θ angles: 7.0±0.2, 7.9±0.2, 12.6±0.2, 14.1±0.2, 18.5±0.2, 20.6±0.2, 21.6±0.2, 35.6±0.2.

In another preferred embodiment of the present invention, X-ray powder diffraction pattern (XRPD) of crystal F further shows characteristic peaks at the following 2θ angles: 7.3±0.2, 12.1±0.2, 14.4±0.2, 16.7±0.2, 19.8±0.2, 21.1±0.2, 22.9±0.2, 23.6±0.2, 24.9±0.2, 30.7±0.2.

In another preferred embodiment of the present invention, X-ray powder diffraction pattern (XRPD) of crystal F further shows characteristic peaks at the following 2θ angles: 15.8±0.2, 18.0±0.2, 19.3±0.2, 25.4±0.2.

In another preferred embodiment of the present invention, crystal F has X-ray powder diffraction pattern (XRPD) shown in FIG. 10.

In another preferred embodiment of the present invention, crystal F has IR spectrogram shown in FIG. 11.

Crystal G of a cyclopeptide of formula I, wherein R represents H or a cation capable of forming a pharmaceutically acceptable salt, and X-ray powder diffraction pattern (XRPD) of crystal F shows characteristic peaks at the following 2θ angles: 7.3±0.2°, 19.8±0.2°, 21.1±0.2°.

Crystal G of a cyclopeptide of formula I, wherein R represents H or a cation capable of forming a pharmaceutically acceptable salt, and X-ray powder diffraction pattern (XRPD) of crystal F shows characteristic peaks at the following 2θ angles: 8.3±0.2°, 12.0±0.2°, 12.9±0.2°, 13.3±0.2°, 14.1±0.2°, 15.3±0.2°, 16.8±0.2°, 18.6±0.2°, 22.7±0.2°, 25.8±0.2°, 26.9±0.2°.

In another preferred embodiment of the present invention, crystal G has X-ray powder diffraction pattern (XRPD) shown in FIG. 12.

In another preferred embodiment of the present invention, crystal G has IR spectrogram shown in FIG. 13.

In another aspect of the invention, a preparation method for the crystals A-G of the cyclopeptide is provided.

A preparation method for crystals A-G of the cyclopeptide includes the following steps:

(a) dissolving the compound of formula I into water or aqueous organic solvent (i), and controlling pH of the solution comprising the compound of formula I;

(b) obtaining the crystal of the cyclopeptide by reducing the temperature and/or adding organic solvent (i).

In step (a), the temperature for dissolution is 10 to 50° C., preferably 20 to 40° C.

In step (a), the volume ratio of organic solvent (i) to water in the aqueous organic solvent (i) is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (a), pH of the solution is controlled at 2.0-5.0, preferably 3.5-4.5.

In step (b), the temperature is reduced to −40 to 35° C., preferably −10 to 35° C., more preferably −5 to 30° C., and the most preferably 5 to 10° C.

In step (b), the volume ratio of organic solvent (i) to the solution of step (a) is 0.1 to 50, preferably 0.1 to 10, and the most preferably 1-5.

In step (a) and/or (b), said organic solvent (i) is one or more selected from the group consisting of methanol, ethanol, n-propanol, and isopropanol.

In one embodiment of the present invention, after step (b), there can be step (c): obtaining the crystals of the cyclopeptide by centrifuging or filtrating.

In one embodiment of the present invention, after step (c), there can be step (d): vacuum-drying for controlling the moisture content, thereby obtaining the crystals.

A preparation method for crystal A of the cyclopeptide includes the following steps:

(a) dissolving the compound of formula I into aqueous organic solvent (i), and controlling pH of the solution comprising the compound of formula I;

(b) obtaining crystal A of the cyclopeptide by reducing the temperature and/or adding organic solvent (i).

In step (a), the temperature for dissolution is 10 to 50° C., preferably 20 to 40° C.

In step (a), the volume ratio of organic solvent (i) to water in the aqueous organic solvent (i) is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (a), pH of the solution is controlled at 2.0-5.0, preferably 3.5-4.5.

In step (b), the temperature is reduced to −40 to 35° C., preferably −10 to 35° C., more preferably −5 to 30° C., and the most preferably 5 to 10° C.

In step (b), the volume ratio of organic solvent (i) to the solution of step (a) is 0.1 to 50, preferably 0.1 to 10, and the most preferably 1-5.

In step (a) and/or (b), said organic solvent (i) is one or more selected from the group consisting of ethanol, n-propanol, and isopropanol.

Furthermore, crystal A of the cyclopeptide can be obtained through the following steps:

(a) dissolving the compound of formula I into water, and controlling pH of the solution comprising the compound of formula I;

(b) completely precipitating crystal A of the compound of formula I by reducing the temperature and adding organic solvent (i), or completely precipitating crystal A of the compound of formula I by adding organic solvent (i).

In step (a), the temperature for dissolution is 10 to 50° C., preferably 20 to 40° C.

In step (a), pH of the solution is controlled at 2.0-5.0, preferably 3.5-4.5.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In step (b), the volume ratio of organic solvent (i) to the solution of step (a) is 0.1 to 50, preferably 0.1 to 10, and the most preferably 1-5.

In step (b), said organic solvent (i) is one or more selected from the group consisting of ethanol, n-propanol, and isopropanol.

In one embodiment of the present invention, crystal A of the compound of formula I can be obtained through the following steps:

(a) dissolving the compound of formula I into aqueous organic solvent (i), and controlling pH of the solution comprising the compound of formula I;

(b) completely precipitating crystal A of the compound of formula I by reducing the temperature and adding organic solvent (i);

(c) obtaining crystal A by centrifuging or filtrating.

In step (a), the temperature for dissolution is 10 to 50° C., preferably 20 to 40° C.

In step (a), pH of the solution is controlled at 2.0-5.0, preferably 3.5-4.5.

In step (a), the volume ratio of organic solvent (i) to water in the aqueous organic solvent (i) is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In step (b), the volume ratio of organic solvent (i) to the solution of step (a) is 0.1 to 50, preferably 0.1 to 10, and the most preferably 1-5.

In steps (a) and (b), said organic solvent (i) is one or more selected from the group consisting of ethanol, n-propanol, and isopropanol.

In one embodiment of the present invention, crystal A of the compound of formula I can be obtained through the following steps:

(a) dissolving the compound of formula I into aqueous organic solvent (i), and controlling pH of the solution comprising the compound of formula I;

(b) completely precipitating crystal A of the compound of formula I by reducing the temperature;

(c) obtaining crystal A by centrifuging or filtrating.

In step (a), the temperature for dissolution is 10 to 50° C., preferably 20 to 40° C.

In step (a), pH of the solution is controlled at 2.0-5.0, preferably 3.5-4.5.

In step (a), the volume ratio of organic solvent (i) to water in the aqueous organic solvent (i) is 0.01 to 100, preferably 0.1 to 10, more preferably 0.5 to 3.0.

In step (a), said organic solvent (i) is one or more selected from the group consisting of ethanol, n-propanol, and isopropanol.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In one embodiment of the present invention, crystal A of the compound of formula I can be obtained through the following steps:

(a) dissolving the compound of formula I into aqueous organic solvent (i), and controlling pH of the solution comprising the compound of formula I;

(b) completely precipitating crystal A of the compound of formula I by adding organic solvent (i);

(c) obtaining crystal A by centrifuging or filtrating.

In step (a), the temperature for dissolution is 10 to 50° C., preferably 20 to 40° C.

In step (a), pH of the solution is controlled at 2.0-5.0, preferably 3.5-4.5.

In step (a), the volume ratio of organic solvent (i) to water in the aqueous organic solvent (i) is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (b), the volume ratio of organic solvent (i) to the solution of step (a) is 0.1 to 50, preferably 0.1 to 10, and the most preferably 1-5.

In steps (a) and (b), said organic solvent (i) is one or more selected from the group consisting of ethanol, n-propanol, and isopropanol.

In another embodiment of the present invention, crystal A of the compound of formula I can be obtained through the following steps:

(a) dissolving the compound of formula I into water, and controlling pH of the solution comprising the compound of formula I;

(b) completely precipitating crystal A of the compound of formula I by reducing the temperature of the solution and adding organic solvent (i);

(c) obtaining crystal A by centrifuging or filtrating.

In step (a), the temperature for dissolution is 10 to 50° C., preferably 20 to 40° C.

In step (a), pH of the solution is controlled at 2.0-5.0, preferably 3.5-4.5.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In step (b), the volume ratio of organic solvent (i) to the solution of step (a) is 0.1 to 50, preferably 0.1 to 10, and the most preferably 1-5.

In step (b), said organic solvent (i) is one or more selected from the group consisting of ethanol, n-propanol, and isopropanol.

In another embodiment of the present invention, crystal A of the compound of formula I can be obtained through the following steps:

(a) dissolving the compound of formula I into water, and controlling pH of the solution comprising the compound of formula I;

(b) completely precipitating crystal A of the compound of formula I by adding organic solvent (i);

(c) obtaining crystal A by centrifuging or filtrating.

In step (a), the temperature for dissolution is 10 to 50° C., preferably 20 to 40° C.

In step (a), pH of the solution is controlled at 2.0-5.0, preferably 3.5-4.5.

In step (a), the solution comprises 50 to 500 mg/ml, preferably 80 to 450 mg/ml, more preferably 100 to 300 mg/ml of compound of formula I, based on the total volume of the solution in step (a).

In step (b), the volume ratio of organic solvent (i) to the solution of step (a) is 0.1 to 50, preferably 0.1 to 10, and the most preferably 1-5.

In step (b), said organic solvent (i) is one or more selected from the group consisting of ethanol, n-propanol, and isopropanol.

A preparation method for crystals B and C of the cyclopeptide includes the following steps:

(a) dissolving the compound of formula I into aqueous organic solvent (i), and controlling pH of the solution comprising the compound of formula I;

(b) obtaining crystal A of the cyclopeptide according to claim 1 or 2 by reducing the temperature and/or adding organic solvent (i);

(c) vacuum-drying crystal A obtained in step (b) and controlling the moisture content, so as to give the crystals.

In step (a), the temperature for dissolution is 10 to 50° C., preferably 20 to 40° C.

In step (a), the volume ratio of organic solvent (i) to water in the aqueous organic solvent (i) is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (a), pH of the solution is controlled at 2.0-5.0, preferably 3.5-4.5.

In step (b), the temperature is reduced to −40 to 35° C., preferably −10 to 35° C., more preferably −5 to 30° C., and the most preferably 5 to 10° C.

In step (b), the volume ratio of organic solvent (i) to the solution of step (a) is 0.1 to 50, preferably 0.1 to 10, and the most preferably 1-5.

In step (a) and/or (b), said organic solvent (i) is one or more selected from the group consisting of ethanol, n-propanol, and isopropanol.

In vacuum-drying of step (c), crystal C of the compound of formula I can be obtained by controlling the moisture content at less than 6%, and crystal B of the compound of formula I can be obtained by controlling the moisture content at 6%-12%.

Furthermore, crystals B and C of the cyclopeptide can be obtained through the following steps:

(a) dissolving the compound of formula I into water, and controlling pH of the solution comprising the compound of formula I;

(b) obtaining crystal A of the cyclopeptide according to claim 1 or 2 by reducing the temperature and adding organic solvent (i), or obtaining crystal A of the cyclopeptide according to claim 1 or 2 by adding organic solvent (i);

(c) vacuum-drying crystal A obtained in step (b) and controlling the moisture content, so as to give the crystals.

In step (a), the temperature for dissolution is 10 to 50° C., preferably 20 to 40° C.

In step (a), the volume ratio of organic solvent (i) to water in the aqueous organic solvent (i) is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (a), pH of the solution is controlled at 2.0-5.0, preferably 3.5-4.5.

In step (b), the temperature is reduced to −40 to 35° C., preferably −10 to 35° C., more preferably −5 to 30° C., and the most preferably 5 to 10° C.

In step (b), the volume ratio of organic solvent (i) to the solution of step (a) is 0.1 to 50, preferably 0.1 to 10, and the most preferably 1-5.

In step (a) and/or (b), said organic solvent (i) is one or more selected from the group consisting of ethanol, n-propanol, and isopropanol.

In vacuum-drying of step (c), crystal C of the compound of formula I can be obtained by controlling the moisture content at less than 6%, and crystal B of the compound of formula I can be obtained by controlling the moisture content at 6%-12%.

In one embodiment of the present invention, crystal B or C of the compound of formula I can be obtained through the following steps:

vacuum-drying crystal A of compound of formula I and controlling the moisture content, so as to give crystal B or C, or the combination thereof.

When vacuum-drying, crystal C of the compound of formula I can be obtained by controlling the moisture content at less than 6%, and crystal B of the compound of formula I can be obtained by controlling the moisture content at 6%-12%.

In another embodiment of the present invention, crystal B of the compound of formula I can be obtained through the following steps:

(a) dissolving the compound of formula I into aqueous organic solvent (i), and controlling pH of the solution comprising the compound of formula I;

(b) completely precipitating crystal A of the cyclopeptide by reducing the temperature and/or adding organic solvent (i);

(c) obtaining crystal A by centrifuging or filtrating;

(d) vacuum-drying crystal A obtained in step (c) and controlling the moisture content at 6%-12%, so as to give crystal B.

In step (a), the temperature for dissolution is 10 to 50° C., preferably 20 to 40° C.

In step (a), pH of the solution is controlled at 2.0-5.0, preferably 3.5-4.5.

In step (a), the volume ratio of organic solvent (i) to water in the aqueous organic solvent (i) is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In step (b), the volume ratio of organic solvent (i) to the solution of step (a) is 0.1 to 50, preferably 0.1 to 10, and the most preferably 1-5.

In step (a) and/or (b), said organic solvent (i) is one or more selected from the group consisting of ethanol, n-propanol, and isopropanol.

In another embodiment of the present invention, crystal B of the compound of formula I can be obtained through the following steps:

(a) dissolving the compound of formula I into water, and controlling pH of the solution comprising the compound of formula I;

(b) completely precipitating crystal A of the cyclopeptide by reducing the temperature and adding organic solvent (i);

(c) obtaining crystal A by centrifuging or filtrating;

(d) vacuum-drying crystal A obtained in step (c) and controlling the moisture content at 6%-12%, so as to give crystal B.

In step (a), the temperature for dissolution is 10 to 50° C., preferably 20 to 40° C.

In step (a), pH of the solution is controlled at 2.0-5.0, preferably 3.5-4.5.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In step (b), the volume ratio of organic solvent (i) to the solution of step (a) is 0.1 to 50, preferably 0.1 to 10, and the most preferably 1-5.

In step (a) and/or (b), said organic solvent (i) is one or more selected from the group consisting of ethanol, n-propanol, and isopropanol.

In another embodiment of the present invention, crystal C of the compound of formula I can be obtained through the following steps:

(a) dissolving the compound of formula I into aqueous organic solvent (i), and controlling pH of the solution comprising the compound of formula I;

(b) completely precipitating crystal A of the cyclopeptide by reducing the temperature and/or adding organic solvent (i);

(c) obtaining crystal A by centrifuging or filtrating;

(d) vacuum-drying crystal A obtained in step (c) and controlling the moisture content at less than 6%, so as to give crystal C.

In step (a), the temperature for dissolution is 10 to 50° C., preferably 20 to 40° C.

In step (a), pH of the solution is controlled at 2.0-5.0, preferably 3.5-4.5.

In step (a), the volume ratio of organic solvent (i) to water in the aqueous organic solvent (i) is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In step (b), the volume ratio of organic solvent (i) to the solution of step (a) is 0.1 to 50, preferably 0.1 to 10, and the most preferably 1-5.

In step (a) and/or (b), said organic solvent (i) is one or more selected from the group consisting of ethanol, n-propanol, and isopropanol.

In another embodiment of the present invention, crystal C of the compound of formula I can be obtained through the following steps:

(a) dissolving the compound of formula I into water, and controlling pH of the solution comprising the compound of formula I;

(b) completely precipitating crystal A of the cyclopeptide by reducing the temperature and adding organic solvent (i), or completely precipitating crystal A by adding organic solvent (i);

(c) obtaining crystal A by centrifuging or filtrating;

(d) vacuum-drying crystal A obtained in step (c) and controlling the moisture content at less than 6%, so as to give crystal C.

In step (a), the temperature for dissolution is 10 to 50° C., preferably 20 to 40° C.

In step (a), pH of the solution is controlled at 2.0-5.0, preferably 3.5-4.5.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In step (b), the volume ratio of organic solvent (i) to the solution of step (a) is 0.1 to 50, preferably 0.1 to 10, and the most preferably 1-5.

In step (a) and/or (b), said organic solvent (i) is one or more selected from the group consisting of ethanol, n-propanol, and isopropanol.

A preparation method for crystal D of the cyclopeptide includes the following steps:

(a) dissolving the compound of formula I into aqueous methanol, and controlling pH of the solution comprising the compound of formula I;

(b) obtaining crystal D of the cyclopeptide by reducing the temperature and/or adding methanol.

In step (a), the temperature for dissolution is 10 to 50° C., preferably 20 to 40° C.

In step (a), pH of the solution is controlled at 2.0-5.0, preferably 3.5-4.5.

In step (a), the volume ratio of methanol to water in the aqueous methanol is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In step (b), the volume ratio of methanol to the solution of step (a) is 0.1 to 50, preferably 0.1 to 10, and the most preferably 1-5.

Crystal D of the cyclopeptide can also be obtained through the following steps:

(a) dissolving the compound of formula I into water, and controlling pH of the solution comprising the compound of formula I;

(b) completely precipitating crystal D of the compound of formula I by reducing the temperature and adding methanol, or completely precipitating crystal D of the compound of formula I by adding methanol.

In step (a), the temperature for dissolution is 10 to 50° C., preferably 20 to 40° C.

In step (a), pH of the solution is controlled at 2.0-5.0, preferably 3.5-4.5.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −5 to 30° C., and the most preferably 5 to 10° C.

In step (b), the volume ratio of methanol to the solution of step (a) is 0.1 to 50, preferably 0.1 to 10, and the most preferably 1-5.

In one embodiment of the present invention, after step (b), there can be step (c): obtaining crystal D of the cyclopeptide by centrifuging or filtrating.

In one embodiment of the present invention, crystal D of the compound of formula I can be obtained through the following steps:

(a) dissolving the compound of formula I into aqueous methanol, and controlling pH of the solution comprising the compound of formula I;

(b) completely precipitating crystal D of the compound of formula I by adding methanol;

(c) obtaining crystal D by centrifuging or filtrating.

In step (a), the temperature for dissolution is 10 to 50° C., preferably 20 to 40° C.

In step (a), pH of the solution is controlled at 2.0-5.0, preferably 3.5-4.5.

In step (a), the volume ratio of methanol to water in the aqueous methanol is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In step (b), the volume ratio of methanol to the solution of step (a) is 0.1 to 50, preferably 0.1 to 10, and the most preferably 1-5.

In one embodiment of the present invention, crystal D of the compound of formula I can be obtained through the following steps:

(a) dissolving the compound of formula I into aqueous methanol, and controlling pH of the solution comprising the compound of formula I;

(b) completely precipitating crystal D of the compound of formula I by reducing the temperature;

(c) obtaining crystal D by centrifuging or filtrating.

In step (a), the temperature for dissolution is 10 to 50° C., preferably 20 to 40° C.

In step (a), pH of the solution is controlled at 2.0-5.0, preferably 3.5-4.5.

In step (a), the volume ratio of methanol to water in the aqueous methanol is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In another embodiment of the present invention, crystal D of the compound of formula I can be obtained through the following steps:

(a) dissolving the compound of formula I into aqueous methanol, and controlling pH of the solution comprising the compound of formula I;

(b) completely precipitating crystal D of the compound of formula I by adding methanol;

(c) obtaining crystal D by centrifuging or filtrating.

In step (a), the temperature for dissolution is 10 to 50° C., preferably 20 to 40° C.

In step (a), pH of the solution is controlled at 2.0-5.0, preferably 3.5-4.5.

In step (a), the volume ratio of methanol to water in the aqueous methanol is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (b), the volume ratio of methanol to the solution of step (a) is 0.1 to 50, preferably 0.1 to 10, and the most preferably 1-5.

In another embodiment of the present invention, crystal D of the compound of formula I can be obtained through the following steps:

(a) dissolving the compound of formula I into water, and controlling pH of the solution comprising the compound of formula I;

(b) completely precipitating crystal D of the compound of formula I by reducing the temperature and adding methanol;

(c) obtaining crystal D by centrifuging or filtrating.

In step (a), the temperature for dissolution is 10 to 50° C., preferably 20 to 40° C.

In step (a), pH of the solution is controlled at 2.0-5.0, preferably 3.5-4.5.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −5 to 30° C., and the most preferably 5 to 10° C.

In step (b), the volume ratio of methanol to the solution of step (a) is 0.1 to 50, preferably 0.1 to 10, and the most preferably 1-5.

In another embodiment of the present invention, crystal D of the compound of formula I can be obtained through the following steps:

(a) dissolving the compound of formula I into water, and controlling pH of the solution comprising the compound of formula I;

(b) completely precipitating crystal D of the compound of formula I by adding methanol;

(c) obtaining crystal D by centrifuging or filtrating.

In step (a), the temperature for dissolution is 10 to 50° C., preferably 20 to 40° C.

In step (a), pH of the solution is controlled at 2.0-5.0, preferably 3.5-4.5.

In step (a), the solution comprises 50 to 500 mg/ml, preferably 80 to 450 mg/ml, more preferably 100 to 300 mg/ml of compound of formula I, based on the total volume of the solution in step (a).

In step (b), the volume ratio of methanol to the solution of step (a) is 0.1 to 50, preferably 0.1 to 10, and the most preferably 1-5.

A preparation method for crystal E of the cyclopeptide includes the following steps:

(a) dissolving the compound of formula I into aqueous methanol, and controlling pH of the solution comprising the compound of formula I;

(b) completely precipitating crystal D of the compound of formula I by reducing the temperature and/or adding methanol;

(c) obtaining crystal D by centrifuging or filtrating;

(d) vacuum-drying crystal D obtained in step (c) and controlling the moisture content at less than 10%, so as to give crystal E.

In step (a), the temperature for dissolution is 10 to 50° C., preferably 20 to 40° C.

In step (a), pH of the solution is controlled at 2.0-5.0, preferably 3.5-4.5.

In step (a), the volume ratio of methanol to water in the aqueous methanol is 0.01 to 100, preferably 0.1 to 10, more preferably 0.5 to 3.0.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In step (b), the volume ratio of methanol to the solution of step (a) is 0.1 to 50, preferably 0.1 to 10, and the most preferably 1-5.

Crystal E of the cyclopeptide can also be obtained through the following steps:

(a) dissolving the compound of formula I into water, and controlling pH of the solution comprising the compound of formula I;

(b) completely precipitating crystal D of the compound of formula I by reducing the temperature and adding methanol, or completely precipitating crystal D by adding methanol;

(c) obtaining crystal D by centrifuging or filtrating;

(d) vacuum-drying crystal D obtained in step (c) and controlling the moisture content at less than 10%, so as to give crystal E.

In step (a), the temperature for dissolution is 10 to 50° C., preferably 20 to 40° C.

In step (a), pH of the solution is controlled at 2.0-5.0, preferably 3.5-4.5.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −40 to 35° C., preferably −10 to 35° C., more preferably −5 to 30° C., and the most preferably 5 to 10° C.

In step (b), the volume ratio of methanol to the solution of step (a) is 0.1 to 50, preferably 0.1 to 10, and the most preferably 1-5.

In another embodiment of the present invention, crystal E of the compound of formula I can be obtained through the following steps:

vacuum-drying crystal D of compound of formula I and controlling the moisture content, so as to give crystal E, or the combination of crystal D and crystal E.

When vacuum-drying, crystal E of the compound of formula I can be obtained by controlling the moisture content at less than 10%.

A preparation method for crystal F of the cyclopeptide includes the following steps:

(a) dissolving the compound of formula I into water, and controlling pH of the solution comprising the compound of formula I;

(b) completely precipitating crystal F of the compound of formula I (the cyclopeptide) by reducing the temperature.

In step (a), the temperature for dissolution is 10 to 50° C., preferably 20 to 40° C.

In step (a), pH of the solution is controlled at 2.0-5.0, preferably 3.5-4.5.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −10 to 35° C., preferably −5 to 30° C., and the most preferably 5 to 10° C.

In one embodiment of the present invention, after step (b), there can be step (c): obtaining crystal F of the cyclopeptide by centrifuging or filtrating.

A preparation method for crystal G of the cyclopeptide includes the following steps:

(a) dissolving the compound of formula I into water, and controlling pH of the solution comprising the compound of formula I;

(b) completely precipitating crystal F of the compound of formula I by reducing the temperature;

(c) obtaining crystal F by centrifuging or filtrating;

(d) vacuum-drying crystal F obtained in step (c) and controlling the moisture content at less than 10%, so as to give crystal G.

In step (a), the temperature for dissolution is 10 to 50° C., preferably 20 to 40° C.

In step (a), pH of the solution is controlled at 2.0-5.0, preferably 3.5-4.5.

In step (a), the solution comprises 50 to 500 mg/ml, preferably 80 to 450 mg/ml, more preferably 100 to 300 mg/ml of compound of formula I, based on the total volume of the solution in step (a).

In step (b), the temperature is reduced to −10 to 35° C., preferably −5 to 30° C., and the most preferably 5 to 10° C.

In another embodiment of the present invention, crystal G of the compound of formula I can be obtained through the following steps:

vacuum-drying crystal F of compound of formula I and controlling the moisture content, so as to give crystal G, or the combination of crystal F and crystal G.

When vacuum-drying, crystal G of the compound of formula I can be obtained by controlling the moisture content at less than 10%.

As used herein, "compound I", "compound of formula I" or "formula I compound" may be used interchangeably, all of which refer to an amorphous substance with chemical structure of formula I or a substance with other crystal form other than crystals A-G of the compound of formula I according to the invention, or a compound having the following structure formula or a pharmaceutically acceptable salt thereof:

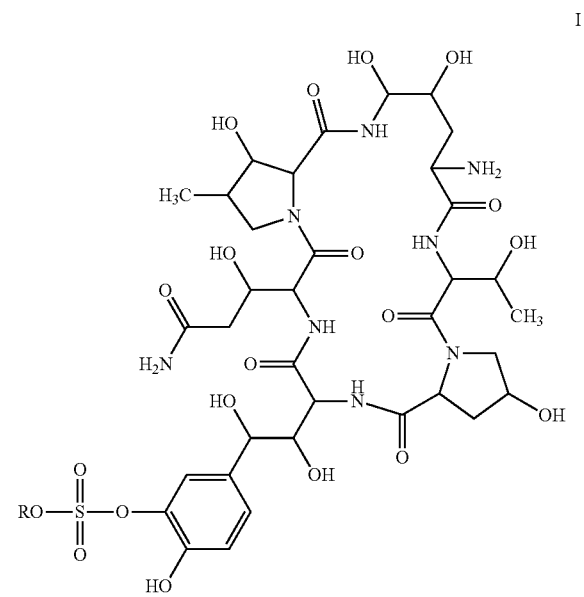

wherein, R represents H or a cation capable of forming a pharmaceutically acceptable salt.

Preferably, pharmaceutically acceptable salts include: metal salts such as alkali metal salts (such as sodium salt, potassium salt), alkaline earth metal salts (such as calcium salt, magnesium salt, etc.), ammonium salts, salts formed with organic bases (e.g., trimethylamine salt, triethylamine salt, pyridine salt, picoline salt, dicyclohexylamine salt, N,N,-dibenzylethylenediamine salt, diisopropylethylamine salt, etc.), organic acid addition salts (such as formate, acetate, trifluoroacetate, maleate, tartrate, methanesulfonate, benzenesulfonate, toluenesulfonate, etc.), inorganic acid addition salts (e.g. hydrochloride, hydrobromide, hydroiodide, sulfate, phosphate, etc.), salts formed with an amino acid (e.g. arginine, aspartic acid, glutamic acid, etc.), and the like.

The compound of formula I can be obtained by conventional methods in the art, for example, but not limited to, the preparation method for this compound reported in WO9611210; alternatively, the compound may also be obtained through commercial sources, such as, but not limited to, such as Fujisawa, Japan.

Identification of the Crystal of Compound of Formula I and Properties Thereof

After obtaining the crystals of compound of formula I, the inventors further studied properties thereof by using a variety of methods and instruments.

At present, X-ray powder diffraction, also known as X-ray polycrystal diffraction, (XRD or XRPD) is the routine experimental method for determining the structure of a crystal (i.e., crystal form). Using X-ray powder diffractometer, a series of diffraction patterns can be produced when X-ray passing through a crystal. In the pattern, different diffraction lines and the intensities thereof are determined by atomic cluster having certain structure, so that the structure of a crystal can be determined.

The methods for determining the X-ray diffraction pattern of a crystal are known in the art. For example, X-ray diffraction pattern can be obtained by using Bruker D8 Advanced Model X-ray powder diffractometer with the scanning rate of 2°/min. Copper irradiated target is used to give the pattern.

The crystal structure can also be determined by Infrared Spectrometry (IR), which is known in the art. For example, it can be determined by using PE Spectrum One B, tableting at KBr:sample=200:1, and scanning with 400~4000 $cm^{-1}$.

Moisture content of a crystal is determined by using common detection methods in the art, for example, Karl Fischer (KF) determination.

Uses of the Crystals of Compound of Formula I and Compositions Thereof

Uses of the crystals of compound of formula I are provided by the invention. In one aspect, it can be used to prepare the compound of formula II;

composition, pharmaceutically acceptable carriers can include liquids such as water, saline, glycerol and ethanol. Additionally, auxiliary substances may be present with these carriers, such as disintegrating agents, wetting agents, emulsifying agents, pH buffering substances and the like.

The advantages of the invention mainly include:

1. In the present invention, the purity of the crystal of compound of formula I has been greatly improved, and the impurities have been greatly reduced, so as to obtain the crystal of compound of formula I with the high purit and stable crystal forms, thereby solving the technical problems to be solved in the art.

2. The inventors have selected particular preparation conditions through repeated experiments, and unexpected technical effects have been produced, so that a preparation method for the crystal of compound of formula I with the high purit is provided, and such method is suitable for large-scale production and of high yield.

3. A method for preparing the high purity compound of formula II with good stability is provided in the present invention, wherein the compound of formula II can be produced from the precursor, compound of formula I. The pressure on the purification of compound II will be greatly released, and the final product, the high purity compound of

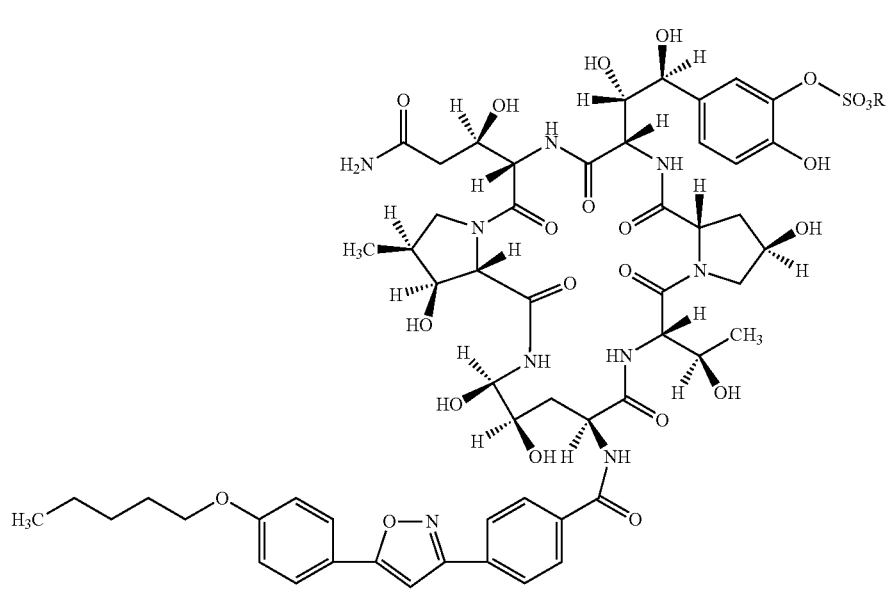

Synthetic routes can be found in WO9611210, 9857923, 2004014879.

In another aspect, the crystals of compound of formula I provided in the present invention can be directly used in preparing medicaments for treating fungal infections. A pharmaceutical composition comprising a crystal of compound of formula I and a pharmaceutically acceptable carrier can be provided.

As used herein, the term "pharmaceutically acceptable carrier" refers to a carrier for administration of a therapeutic agent, including various excipients and diluents. The term refers to such carriers that they themselves are not necessary active ingredients, and won't produce undue toxicity upon administration. Suitable carriers are well-known to the skilled person in the art. In "Remington's Pharmaceutical Sciences" (Mack Pub. Co., NJ 1991), a full discussion on pharmaceutically acceptable excipients can be found. In the formula II can be obtained by a simple purification process. The yield is also greatly improved, thereby achieving unexpected technical effects.

BRIEF DESCRIPTION OF THE DRAWINGS

FIG. 1 is X-ray powder diffraction pattern of crystal A of compound of Formula I; wherein

| Peak No. | 2-θ | d (A) | I % (relative intensity) |
|---|---|---|---|
| 1 | 7.080 | 12.4748 | 100 |
| 2 | 7.339 | 12.0352 | 30.0 |
| 3 | 8.040 | 10.9882 | 56.7 |
| 4 | 9.080 | 9.7318 | 11.0 |
| 5 | 10.379 | 8.5160 | 10.6 |

-continued

| Peak No. | 2-θ | d (A) | I % (relative intensity) |
|---|---|---|---|
| 6 | 11.840 | 7.4681 | 24.8 |
| 7 | 12.319 | 7.1789 | 34.3 |
| 8 | 12.861 | 6.8777 | 26.6 |
| 9 | 13.540 | 6.5343 | 15.1 |
| 10 | 14.381 | 6.1537 | 25.2 |
| 11 | 14.720 | 6.0131 | 42.4 |
| 12 | 15.079 | 5.8705 | 18.3 |
| 13 | 16.139 | 5.4873 | 30.3 |
| 14 | 16.799 | 5.2732 | 57.3 |
| 15 | 18.540 | 4.7817 | 42.7 |
| 16 | 18.920 | 4.6866 | 53.3 |
| 17 | 19.600 | 4.5255 | 29.9 |
| 18 | 20.360 | 4.3582 | 66.5 |
| 19 | 21.141 | 4.1990 | 52.1 |
| 20 | 22.141 | 4.0115 | 39.0 |
| 21 | 22.780 | 3.9005 | 48.7 |
| 22 | 23.160 | 3.8372 | 50.0 |
| 23 | 24.360 | 3.6509 | 45.4 |
| 24 | 24.819 | 3.5844 | 25.2 |
| 25 | 25.440 | 3.4983 | 41.7 |
| 26 | 25.961 | 3.4293 | 28.6 |
| 27 | 26.961 | 3.3043 | 17.3 |
| 28 | 27.740 | 3.2132 | 28.4 |
| 29 | 28.319 | 3.1488 | 24.2 |
| 30 | 28.800 | 3.0974 | 19.8 |
| 31 | 29.221 | 3.0537 | 17.7 |
| 32 | 29.861 | 2.9897 | 18.2 |
| 33 | 31.440 | 2.8430 | 27.2 |
| 34 | 33.540 | 2.6697 | 22.1 |
| 35 | 34.040 | 2.6316 | 17.2 |
| 36 | 34.700 | 2.5830 | 15.3 |
| 37 | 37.680 | 2.3853 | 17.9 |
| 38 | 38.420 | 2.3411 | 16.2 |
| 39 | 39.480 | 2.2806 | 14.9 |
| 40 | 40.480 | 2.2265 | 15.1 |

Figure 2:
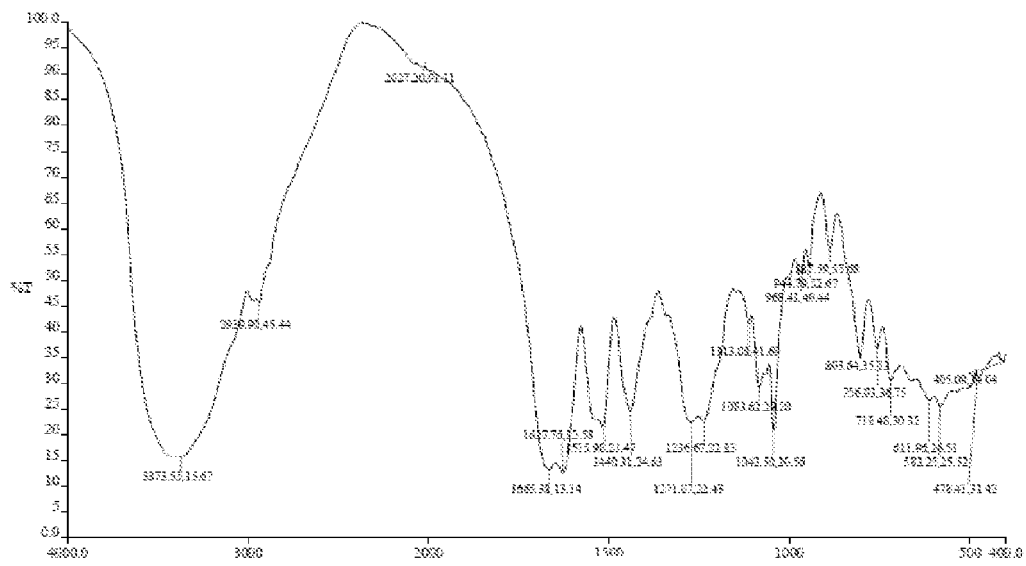

FIG. 2 is infrared (IR) spectrum of crystal A of compound of Formula I.

Figure 3:
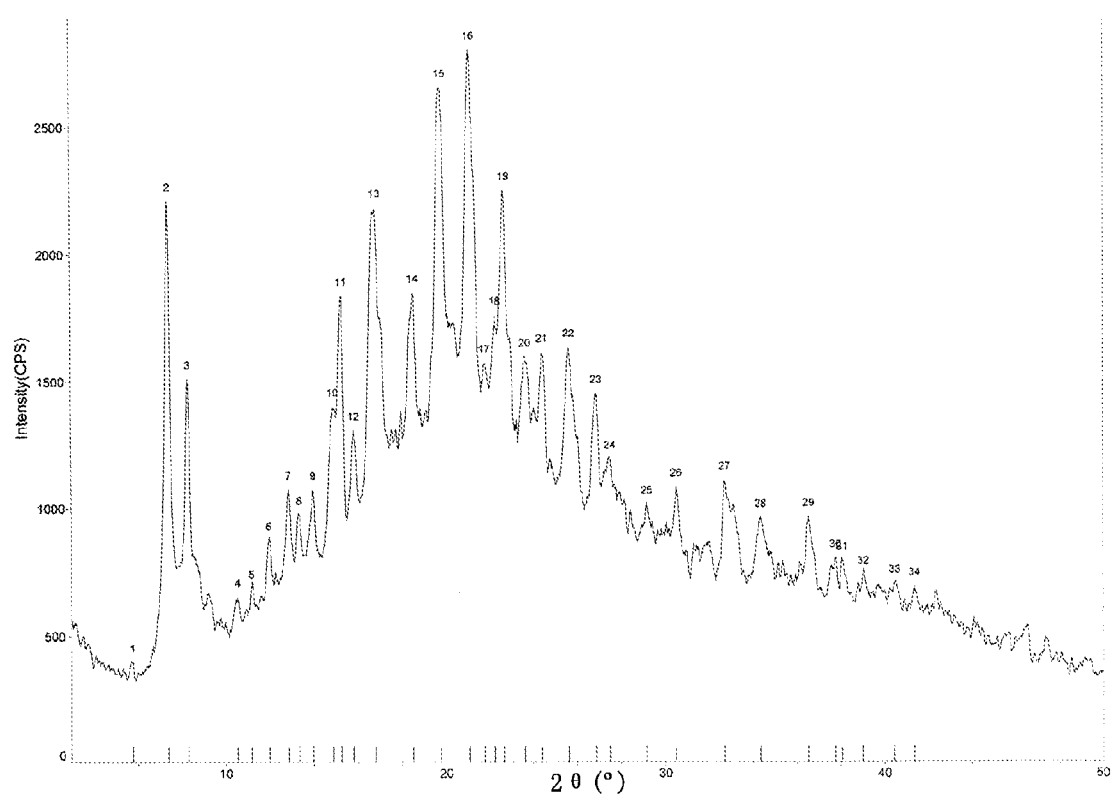

FIG. 3 is X-ray powder diffraction pattern of crystal B of compound of Formula I; wherein

| Peak No. | 2-θ | d(A) | I % (relative intensity) |
|---|---|---|---|
| 1 | 5.772 | 15.2981 | 14.0 |
| 2 | 7.342 | 11.9359 | 78.6 |
| 3 | 8.301 | 10.6432 | 53.6 |
| 4 | 10.560 | 8.3707 | 23.0 |
| 5 | 11.188 | 7.9022 | 24.2 |
| 6 | 11.945 | 7.3808 | 30.9 |
| 7 | 12.820 | 6.8676 | 38.0 |
| 8 | 13.359 | 6.6224 | 34.5 |
| 9 | 13.981 | 6.3293 | 38.0 |
| 10 | 14.881 | 5.9484 | 49.7 |
| 11 | 15.278 | 5.7945 | 65.2 |
| 12 | 15.821 | 5.5970 | 46.3 |
| 13 | 16.799 | 5.2731 | 77.6 |
| 14 | 18.520 | 4.7868 | 65.7 |
| 15 | 19.650 | 4.4893 | 94.6 |
| 16 | 21.060 | 4.2149 | 100.0 |
| 17 | 21.761 | 4.0807 | 55.7 |
| 18 | 22.140 | 3.9903 | 62.5 |
| 19 | 22.773 | 3.9186 | 80.0 |
| 20 | 23.640 | 3.7605 | 56.6 |
| 21 | 24.341 | 3.6419 | 57.2 |
| 22 | 25.440 | 3.4715 | 58.0 |
| 23 | 26.879 | 3.3141 | 51.5 |
| 24 | 27.499 | 3.2408 | 42.3 |
| 25 | 29.142 | 3.0618 | 35.9 |
| 26 | 30.482 | 2.9302 | 38.3 |
| 27 | 32.700 | 2.7363 | 39.3 |
| 28 | 34.340 | 2.6093 | 34.0 |
| 29 | 36.520 | 2.4584 | 34.2 |
| 30 | 37.761 | 2.3804 | 28.4 |
| 31 | 38.061 | 2.3623 | 28.1 |
| 32 | 39.007 | 2.3072 | 26.0 |
| 33 | 40.463 | 2.2274 | 24.8 |
| 34 | 41.380 | 2.1802 | 24.4 |

Figure 4:
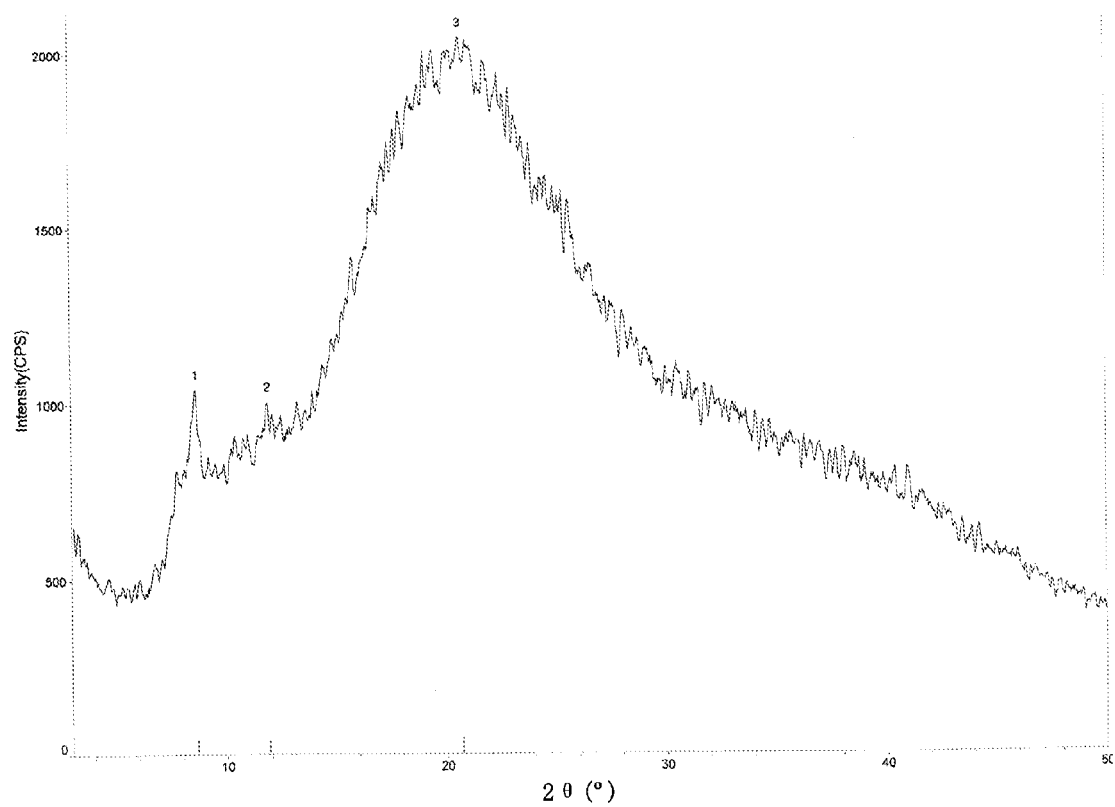

FIG. 4 is X-ray powder diffraction pattern of crystal C of compound of Formula I; wherein

| Peak No. | 2-θ | d (A) | I % (relative intensity) |
|---|---|---|---|
| 1 | 8.640 | 10.2027 | 50.8 |
| 2 | 11.917 | 7.4200 | 49.1 |
| 3 | 20.720 | 4.2833 | 100.0 |

Figure 5:
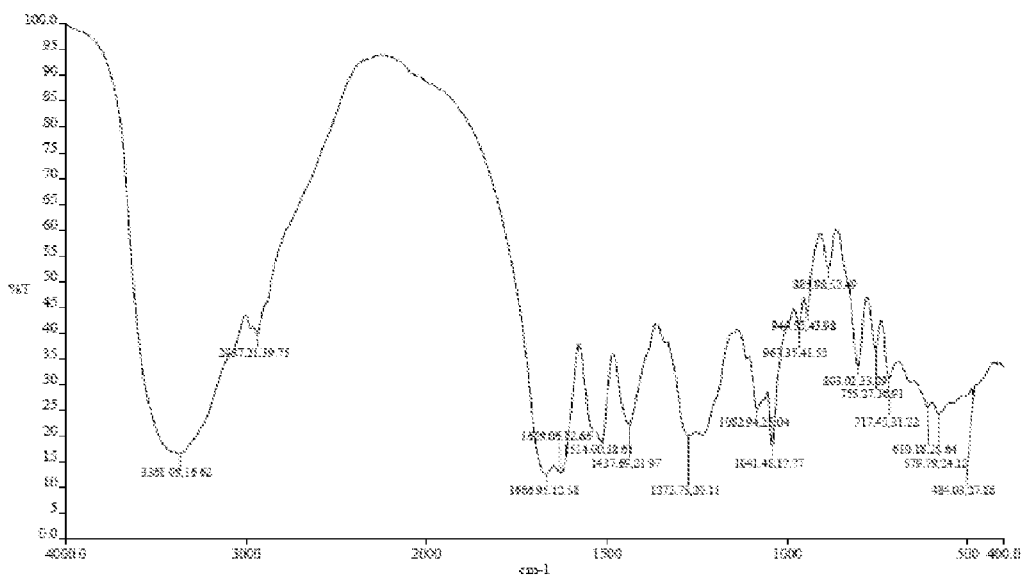

FIG. 5 is infrared (IR) spectrum of crystal C of compound of Formula 1.

Figure 6:
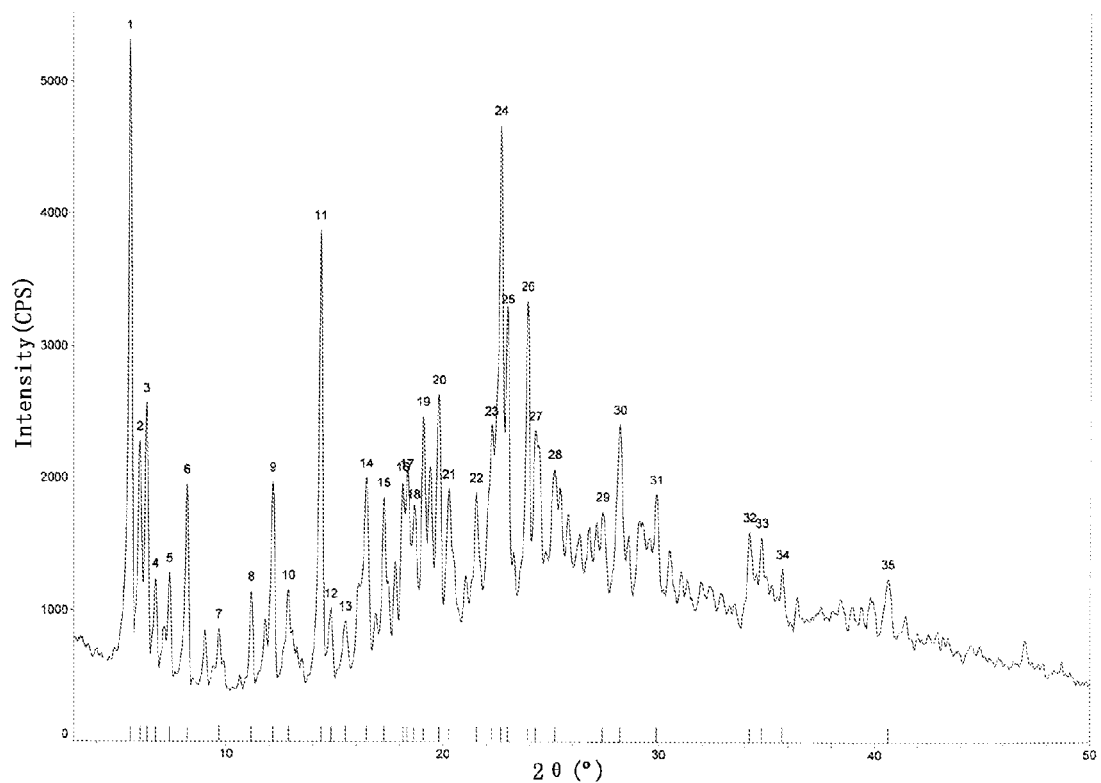

FIG. 6 is X-ray powder diffraction pattern of crystal D of compound of Formula I; wherein

| Peak No. | 2-θ | d(A) | I % (relative intensity) |
|---|---|---|---|
| 1 | 5.579 | 15.8267 | 100.0 |
| 2 | 6.019 | 14.6712 | 42.6 |
| 3 | 6.339 | 13.9319 | 48.0 |
| 4 | 6.739 | 13.1065 | 23.2 |
| 5 | 7.380 | 11.9690 | 23.9 |
| 6 | 8.199 | 10.7744 | 36.5 |
| 7 | 9.679 | 9.1304 | 16.0 |
| 8 | 11.161 | 7.9214 | 21.3 |
| 9 | 12.160 | 7.2724 | 36.8 |
| 10 | 12.879 | 6.8680 | 21.6 |
| 11 | 14.379 | 6.1548 | 72.7 |
| 12 | 14.839 | 5.9649 | 18.9 |
| 13 | 15.500 | 5.7120 | 17.1 |
| 14 | 16.480 | 5.3745 | 37.4 |
| 15 | 17.280 | 5.1274 | 34.6 |
| 16 | 18.159 | 4.8811 | 36.8 |
| 17 | 18.342 | 4.8328 | 37.3 |
| 18 | 18.663 | 4.7505 | 32.9 |
| 19 | 19.101 | 4.6425 | 46.1 |
| 20 | 19.819 | 4.4760 | 49.3 |
| 21 | 20.280 | 4.3753 | 35.8 |
| 22 | 21.539 | 4.1222 | 35.3 |
| 23 | 22.241 | 3.9937 | 44.8 |
| 24 | 22.661 | 3.9207 | 87.7 |
| 25 | 22.978 | 3.8673 | 60.8 |
| 26 | 23.920 | 3.7170 | 62.6 |
| 27 | 24.300 | 3.6598 | 44.1 |
| 28 | 25.200 | 3.5311 | 38.7 |
| 29 | 27.421 | 3.2499 | 32.6 |
| 30 | 28.219 | 3.1597 | 45.0 |
| 31 | 29.899 | 2.9859 | 35.1 |
| 32 | 34.219 | 2.6182 | 29.8 |
| 33 | 34.778 | 2.5774 | 29.0 |
| 34 | 35.740 | 2.5102 | 24.6 |
| 35 | 40.620 | 2.2192 | 23.3 |

Figure 7:
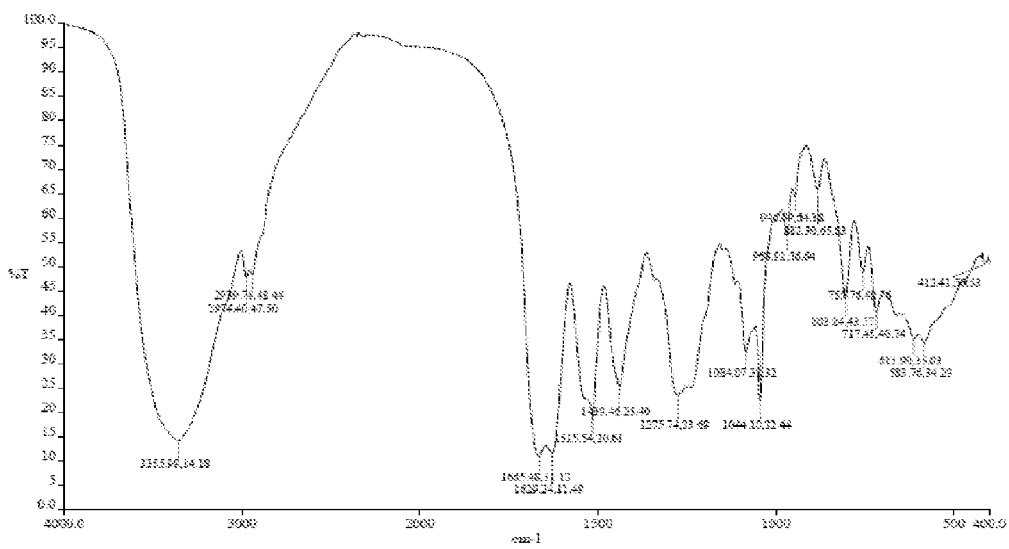

FIG. 7 is infrared (IR) spectrum of crystal D of compound of Formula I.

Figure 8:
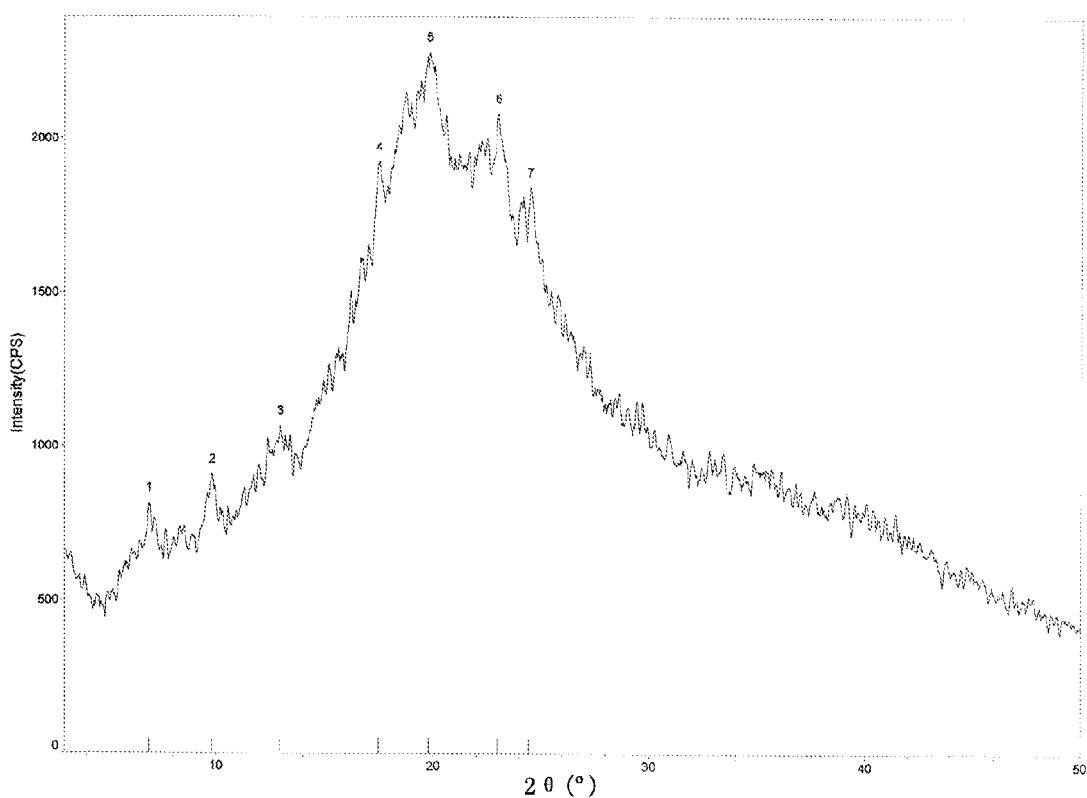

FIG. 8 is X-ray powder diffraction pattern of crystal E of compound of Formula I; wherein

| Peak No. | 2-θ | d (A) | I % (relative intensity) |
|---|---|---|---|
| 1 | 6.881 | 12.8362 | 35.5 |
| 2 | 9.769 | 9.0184 | 39.6 |
| 3 | 12.939 | 6.8361 | 46.6 |
| 4 | 17.478 | 5.0697 | 84.1 |
| 5 | 19.801 | 4.4800 | 100.0 |
| 6 | 22.979 | 3.8671 | 91.1 |
| 7 | 24.462 | 3.6359 | 80.5 |

Figure 9:
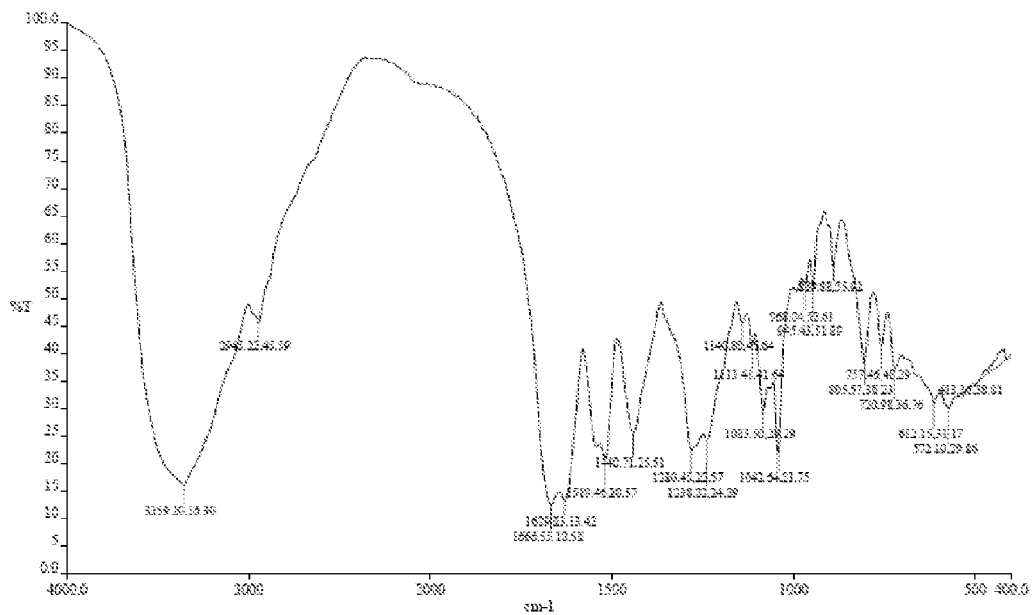

FIG. 9 is infrared (IR) spectrum of crystal E of compound of Formula I.

Figure 10:
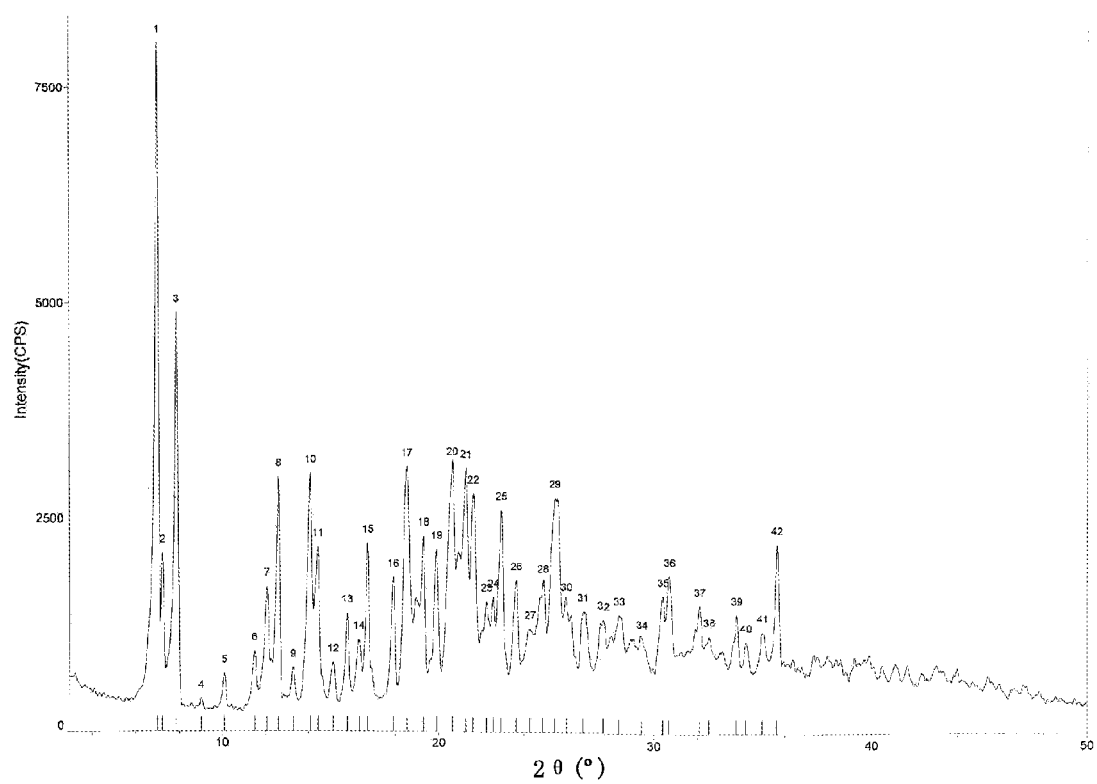

FIG. 10 is X-ray powder diffraction pattern of crystal F of compound of Formula I; wherein

| Peak No. | 2-θ | d(A) | I % (relative intensity) |
|---|---|---|---|
| 1 | 6.999 | 12.6187 | 100.0 |
| 2 | 7.240 | 12.1995 | 25.9 |
| 3 | 7.881 | 11.2088 | 60.7 |
| 4 | 9.021 | 9.7950 | 4.7 |
| 5 | 10.101 | 8.7498 | 8.4 |
| 6 | 11.520 | 7.6750 | 11.7 |
| 7 | 12.081 | 7.3200 | 21.0 |
| 8 | 12.620 | 7.0087 | 36.8 |
| 9 | 13.299 | 6.6519 | 9.3 |
| 10 | 14.099 | 6.2765 | 37.4 |
| 11 | 14.439 | 6.1292 | 26.7 |
| 12 | 15.140 | 5.8471 | 10.0 |
| 13 | 15.781 | 5.6111 | 17.2 |
| 14 | 16.320 | 5.4269 | 13.4 |
| 15 | 16.718 | 5.2985 | 27.3 |
| 16 | 17.901 | 4.9510 | 22.4 |
| 17 | 18.520 | 4.7869 | 38.3 |
| 18 | 19.300 | 4.5952 | 28.3 |
| 19 | 19.900 | 4.4580 | 26.4 |
| 20 | 20.641 | 4.2995 | 38.5 |
| 21 | 21.280 | 4.1718 | 38.2 |
| 22 | 21.620 | 4.1069 | 34.5 |
| 23 | 22.261 | 3.9902 | 19.1 |
| 24 | 22.578 | 3.9348 | 19.6 |
| 25 | 22.940 | 3.8736 | 32.2 |
| 26 | 23.639 | 3.7606 | 22.1 |
| 27 | 24.280 | 3.6628 | 15.1 |
| 28 | 24.862 | 3.5784 | 21.8 |
| 29 | 25.401 | 3.5037 | 34.0 |
| 30 | 25.958 | 3.4297 | 19.2 |
| 31 | 26.721 | 3.3335 | 17.7 |
| 32 | 27.660 | 3.2224 | 16.6 |
| 33 | 28.380 | 3.1422 | 17.3 |
| 34 | 29.438 | 3.0317 | 13.9 |
| 35 | 30.399 | 2.9379 | 20.1 |
| 36 | 30.699 | 2.9100 | 23.0 |
| 37 | 32.099 | 2.7861 | 18.8 |
| 38 | 32.520 | 2.7510 | 14.4 |
| 39 | 33.760 | 2.6527 | 17.4 |
| 40 | 34.200 | 2.6196 | 13.5 |
| 41 | 34.960 | 2.5644 | 14.9 |
| 42 | 35.622 | 2.5183 | 27.5 |

Figure 11:
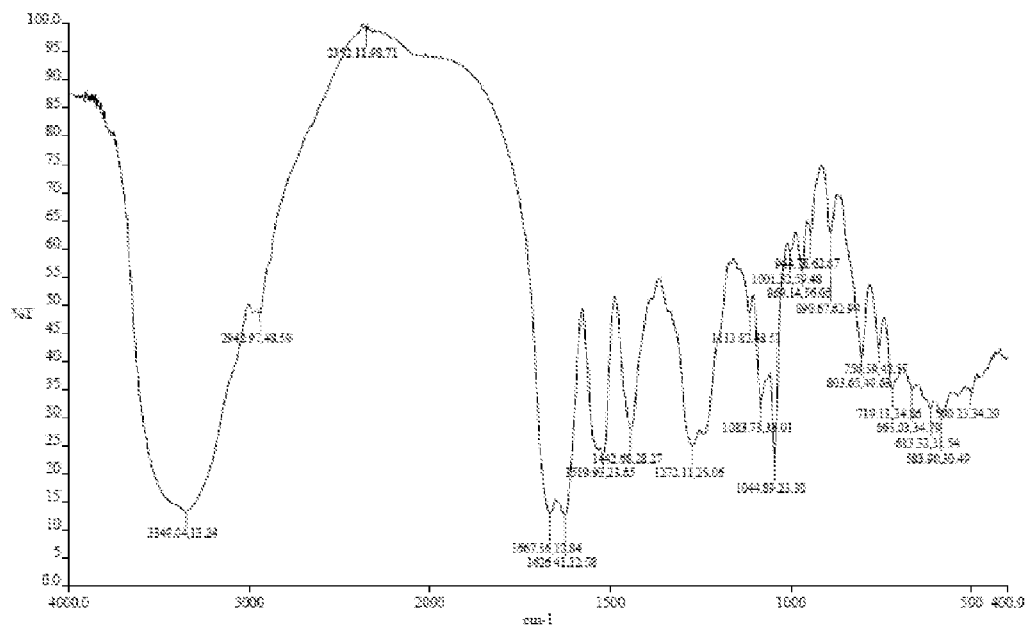

FIG. 11 is infrared (IR) spectrum of crystal F of compound of Formula I.

Figure 12:
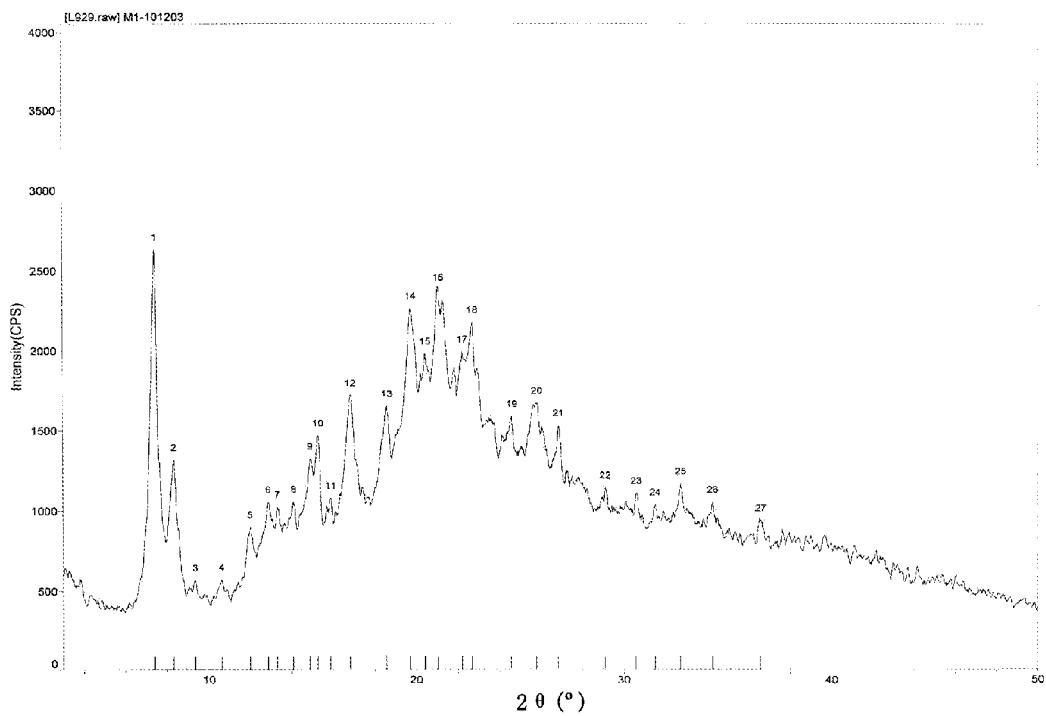

FIG. 12 is X-ray powder diffraction pattern of crystal G of compound of Formula I; wherein

| Peak No. | 2-θ | d(A) | I % (relative intensity) |
|---|---|---|---|
| 1 | 7.320 | 11.9038 | 100.0 |
| 2 | 8.320 | 10.6180 | 49.8 |
| 3 | 9.360 | 9.4412 | 21.4 |
| 4 | 10.620 | 8.3237 | 21.5 |
| 5 | 11.982 | 7.3804 | 33.9 |
| 6 | 12.860 | 6.8779 | 39.8 |
| 7 | 13.301 | 6.6511 | 38.7 |
| 8 | 14.080 | 6.2848 | 39.9 |
| 9 | 14.881 | 5.9482 | 50.0 |
| 10 | 15.260 | 5.8015 | 55.5 |
| 11 | 15.881 | 5.5758 | 40.8 |
| 12 | 16.820 | 5.2666 | 65.2 |
| 13 | 18.579 | 4.7718 | 62.8 |
| 14 | 19.820 | 4.4982 | 68.0 |
| 15 | 20.420 | 4.3456 | 75.1 |
| 16 | 21.059 | 4.2151 | 90.4 |
| 17 | 22.201 | 4.0009 | 75.6 |
| 18 | 22.679 | 3.9175 | 82.6 |
| 19 | 24.577 | 3.6191 | 60.1 |
| 20 | 25.780 | 3.4529 | 63.3 |
| 21 | 26.823 | 3.3210 | 58.0 |
| 22 | 29.085 | 3.0677 | 43.2 |
| 23 | 30.585 | 2.9205 | 42.0 |
| 24 | 31.500 | 2.8378 | 39.2 |
| 25 | 32.740 | 2.7330 | 44.2 |
| 26 | 34.280 | 2.6137 | 39.9 |
| 27 | 36.579 | 2.4545 | 35.6 |

Figure 13:
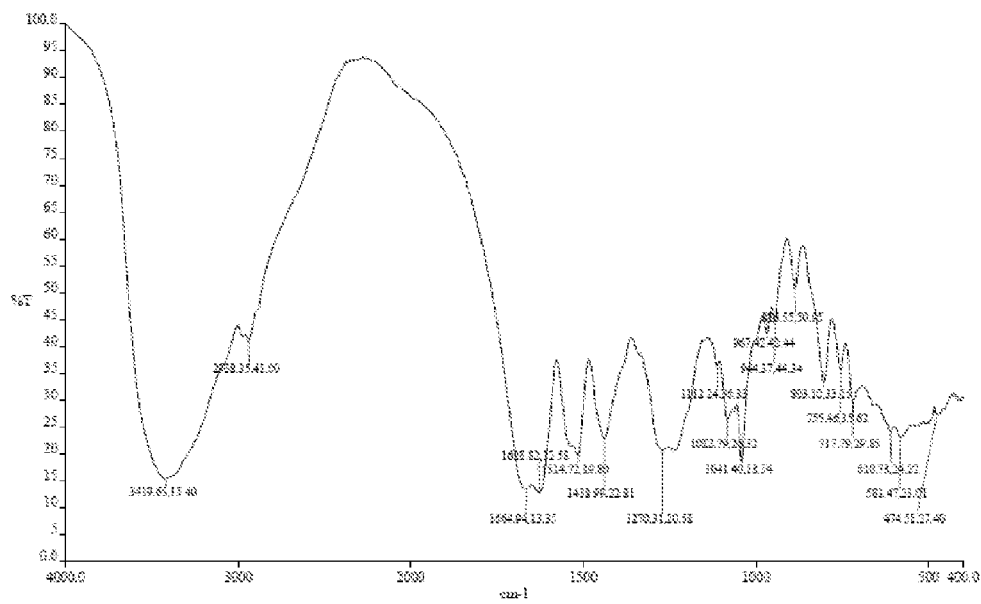

FIG. 13 is infrared (IR) spectrum of crystal G of compound of Formula I.

Figure 14:
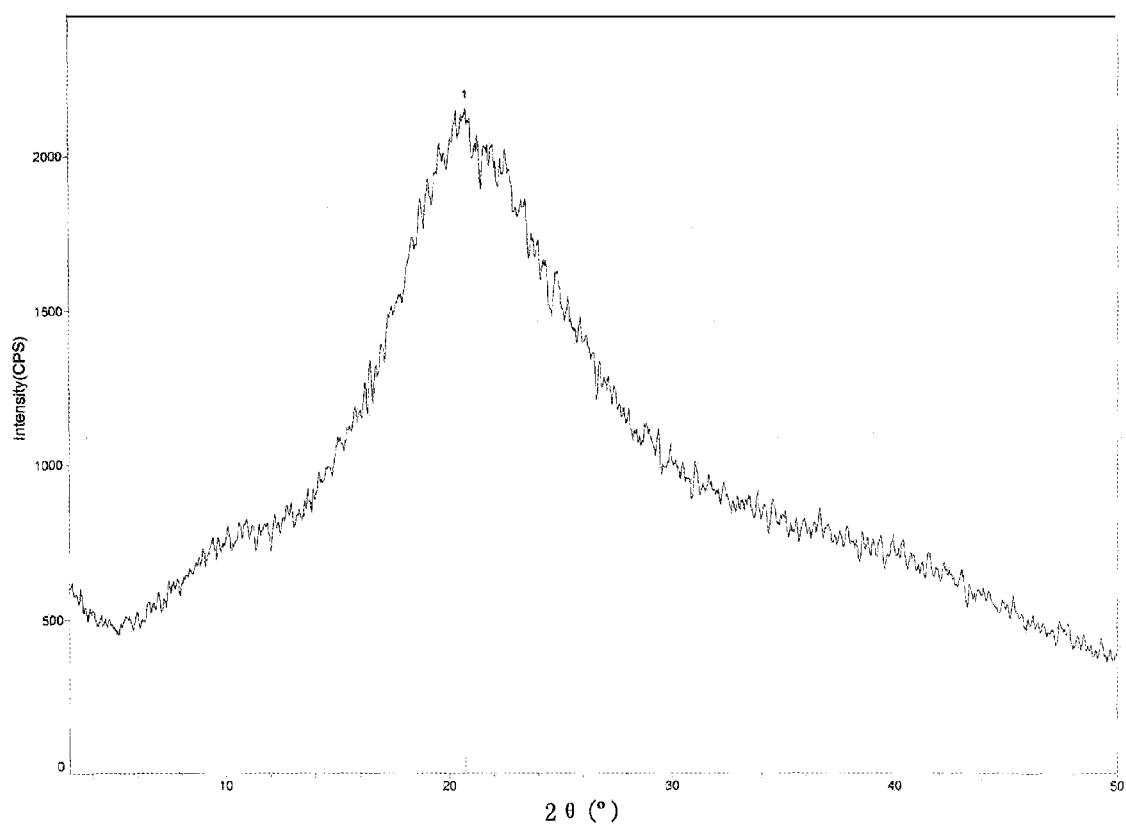

FIG. 14 is X-ray powder diffraction pattern of amorphous powder of compound of Formula I.

THE MODE FOR CARRYING OUT THE INVENTION

The invention will be further illustrated with reference to the following specific examples. It is to be understood that these examples are only intended to illustrate the invention, but not to limit the scope of the invention. For the experimental methods in the following examples without particular conditions, they are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

Example 1

Preparation of Compound I 76 g of the compound of formula I in solid powder was prepared according to the method of Example 1 in U.S. Pat. No. 5,376,634 (see FIG. 14 for XRPD pattern).

Example 2

Preparation of Crystal A of the Compound of Formula I

Figure 1:
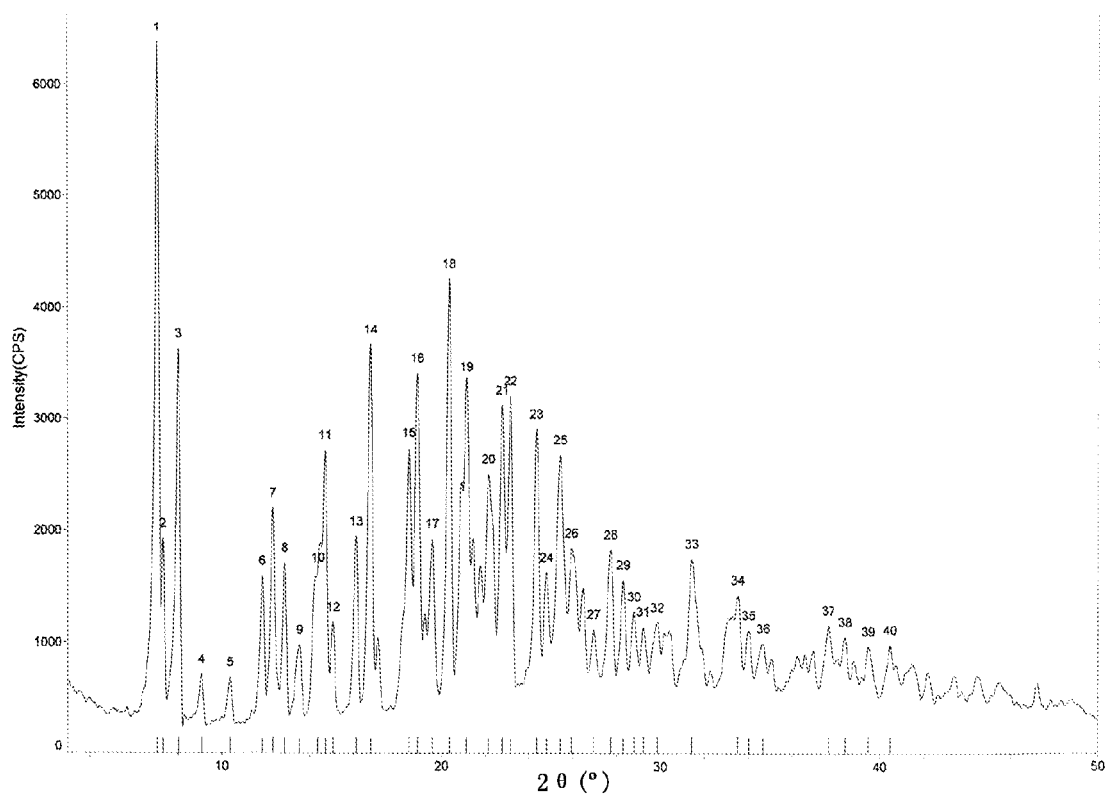

At 50° C., 3.5 g of solid powder of compound I prepared in Example 1 was dissolved into a mixed solution consisting of 5 ml of water and 3 ml of n-propanol and stirred to completely dissolve compound I. pH was adjusted to 2.0 by using glacial acetic acid, and the solution was cooled to 30° C. Crystals of compound I precipitated, and the system was stirred for 5 hours at 30° C., so that the crystals of compound I gradually grew. Crystal A of compound of formula I was obtained by filtration, and XRPD, IR spectra thereof can be found in FIGS. 1-2.

Example 3

Preparation of Crystal A of the Compound of Formula I

At 10° C., 1.5 g of solid powder of compound I prepared in Example 1 was dissolved into a mixed solution consisting of 20 ml of water and 10 ml of n-propanol and stirred to completely dissolve compound I. pH was adjusted to 5.0 by using glacial acetic acid, and 40 ml of n-propanol was slowly added dropwise. And then, the solution was cooled to −5° C. The solution was stirred at −5° C. for 2 hours. Crystal A of compound of formula I was obtained by filtration, and XRPD, IR spectra thereof can be found in FIGS. 1-2.

Example 4

Preparation of Crystal A of the Compound of Formula I

At 30° C., 1.6 g of compound I prepared in Example 1 was dissolved into 9 ml of water, and stirred to completely dissolve compound I. pH was adjusted to 2.8 by using glacial acetic acid, and the solution was cooled to 11° C. Crystals of compound I precipitated, and 61 ml of ethanol was slowly added dropwise. The solution was stirred at 11° C. for 2 hours. Crystal A of compound of formula I was obtained by filtration, and XRPD, IR spectra thereof can be found in FIGS. 1-2.

Example 5

Preparation of Crystal A of the Compound of Formula I

At 28° C., 1.8 g of compound I prepared in Example 1 was dissolved into 5 ml of water, and stirred to completely dissolve compound I. pH was adjusted to 3.6 by using glacial acetic acid, and 30 ml of n-propanol was slowly added dropwise at 28° C. Crystals of compound I precipitated. Crystal A of compound of formula I was obtained by filtration, and XRPD, IR spectra thereof can be found in FIGS. 1-2.

Example 6

Preparation of Crystal A of the Compound of Formula I

At 30° C., 2.8 g of compound I prepared in Example 1 was dissolved into 7 ml of 0.02 mol/L sodium acetate buffer (pH 4.0), and stirred to completely dissolve compound I. pH was adjusted to 4.0 by using glacial acetic acid, and 14 ml of n-propanol was slowly added dropwise. Crystals of compound I precipitated, and the system was stirred for 10 hours at 30° C., so that the crystals of compound I gradually grew. Crystal A of compound of formula I was obtained by filtration using Büchner funnel, and XRPD, IR spectra thereof can be found in FIGS. 1-2.

Example 7

Preparation of Crystal B of the Compound of Formula I

At 30° C., 2.5 g of compound I prepared in Example 1 was dissolved into a mixed solution consisting of 9 ml of water and 7 ml of n-propanol, and stirred to completely dissolve compound I. pH was adjusted to 4.0 by using glacial acetic acid, and the solution was cooled to 10° C. Crystals of compound I precipitated, and 16 ml of n-propanol was slowly added dropwise. The solution was stirred at 10° C. for 2 hours. The crystals were obtained by filtration and vacuum-dried (wherein $P_2O_5$ was placed in vacuum oven). Crystal B of the compound of formula I was obtained when the moisture content was detected as 6.2%, and XRPD thereof can be found in FIG. 3.

Example 8

Preparation of Crystal B of the Compound of Formula I

At 45° C., 1.6 g of compound I prepared in Example 1 was dissolved into a mixed solution consisting of 3 ml of water and 2 ml of ethanol, and stirred to completely dissolve compound I. pH was adjusted to 3.2 by using glacial acetic acid, and the solution was cooled to 30° C. Crystals of compound I precipitated, the system was cooled to 10° C. And then 25 ml of ethanol was slowly added dropwise. The resulting mixture was stirred at 10° C. for 2 hours. The crystals were obtained by filtration and vacuum-dried (wherein $P_2O_5$ was placed in vacuum oven). Crystal B of the compound of formula I was obtained when the moisture content was detected as 9.0%, and XRPD thereof can be found in FIG. 3.

Example 9

Preparation of Crystal B of the Compound of Formula I

At 28° C., 1.8 g of compound I prepared in Example 1 was dissolved into a mixed solution consisting of 5 ml of water and 5 ml of isopropanol, and stirred to completely dissolve compound I. pH was adjusted to 3.6 by using glacial acetic acid, and the solution was cooled to 17° C. Crystals of compound I precipitated, the system was stirred at 17° C. for 2 hours. The crystals were obtained by filtration and vacuum-dried (wherein $P_2O_5$ was placed in vacuum oven). Crystal B of the compound of formula I was obtained when the moisture content was detected as 10.1%, and XRPD thereof can be found in FIG. 3.

Example 10

Preparation of Crystal B of the Compound of Formula I

Crystal A obtained in Example 2 was vacuum-dried (wherein $P_2O_5$ was placed in vacuum oven). Crystal B of the compound of formula I was obtained when the moisture content was detected as 11.9%, and XRPD thereof can be found in FIG. 3.

Example 11

Preparation of Crystal C of the Compound of Formula I

Crystal B obtained in Example 7 was further vacuum-dried (wherein $P_2O_5$ was placed in vacuum oven) for removing moisture. Crystal C of the compound of formula I was obtained when the moisture content was detected as 5.1%, and XRPD and IR spectra thereof can be found in FIGS. 4-5.

Example 12

Preparation of Crystal C of the Compound of Formula I

Crystal B obtained in Example 8 was further vacuum-dried (wherein $P_2O_5$ was placed in vacuum oven) for removing moisture. Crystal C of the compound of formula I was obtained when the moisture content was detected as 5.9%, and XRPD and IR spectra thereof can be found in FIGS. 4-5.

Example 13

Preparation of Crystal C of the Compound of Formula I

Crystal B obtained in Example 9 was further vacuum-dried (wherein $P_2O_5$ was placed in vacuum oven) for removing moisture. Crystal C of the compound of formula I was obtained when the moisture content was detected as 4.1%, and XRPD and IR spectra thereof can be found in FIGS. 4-5.

Example 14

Preparation of Crystal C of the Compound of Formula I

At 30° C., 2.8 g of solid powder of compound I prepared in Example 1 was dissolved into 7 ml of 0.02 mol/L sodium acetate buffer (pH 4.0), and stirred to completely dissolve compound I. pH was adjusted to 4.0 by using glacial acetic acid, and 14 ml of n-propanol was slowly added dropwise. Crystals of compound I precipitated, and the system was stirred for 10 hours at 30° C., so that the crystals of compound I gradually grew. And then the solution was cooled to 10° C., and stirred for 3 hours. Crystals of compound of formula I was obtained by filtration using Büchner funnel, and vacuum-dried (wherein $P_2O_5$ was placed in vacuum oven) for removing moisture. Crystal C of the compound of formula I was obtained when the moisture content was detected as 4.5%, and XRPD IR spectra thereof can be found in FIGS. 4-5.

Example 15

Preparation of Crystal D of the Compound of Formula I

At 25° C., 2.0 g of compound I prepared in Example 1 was dissolved into a mixed solution consisting of 5 ml of water and 15 ml of methanol, and stirred to completely dissolve compound I. pH was adjusted to 3.5 by using glacial acetic acid, and the solution was cooled to 10° C. Crystals of compound I precipitated, and the system was cooled to −40° C. and stirred for 2 hours at −40° C. Crystal D of compound of formula I was obtained by filtration, and XRPD, IR spectra thereof can be found in FIGS. 6-7.

Example 16

Preparation of Crystal E of the Compound of Formula I

At 40° C., 2.1 g of compound I prepared in Example 1 was dissolved into a mixed solution consisting of 5 ml of water and 16 ml of methanol, and stirred to completely dissolve compound I. pH was adjusted to 3.5 by using glacial acetic acid. The solution was cooled to 12° C., and crystals of compound I precipitated. And then 60 ml of methanol was slowly added, and the resulting system was stirred at 12° C. for 2 hours. The crystals were obtained by filtration and vacuum-dried (wherein $P_2O_5$ was placed in vacuum oven). Crystal E of the compound of formula I was obtained when the moisture content was detected as 9.5%, and XRPD, IR spectra thereof can be found in FIGS. 8-9.

Example 17

Preparation of Crystal F of the Compound of Formula I

At 40° C., 2.5 g of compound I prepared in Example 1 was dissolved into 5 ml of water, and stirred to completely dissolve compound I. pH was adjusted to 3.9 by using glacial acetic acid. The solution was cooled to 35° C., and crystals of compound I precipitated. The resulting system was stirred at 35° C. for 10 hours. Crystal F was obtained by filtration, and XRPD, IR spectra thereof can be found in FIGS. 10-11.

Example 18

Preparation of Crystal G of the Compound of Formula I

At 20° C., 0.23 g of compound I prepared in Example 1 was dissolved into 5 ml of water, and stirred to completely dissolve compound I. pH was adjusted to 3.9 by using glacial acetic acid. The solution was cooled to 5° C., and crystals of compound I precipitated. The resulting system was stirred at 5° C. for 10 hours. The crystals were obtained by filtration and vacuum-dried (wherein $P_2O_5$ was placed in vacuum oven). Crystal G of the compound of formula I was obtained when the moisture content was detected as 9.8%, and XRPD, IR spectra thereof can be found in FIGS. 12-13.

Example 19

Preparation of the Compound of Formula II from the Crystal of Compound of Formula I The compound of formula II was synthesized from the compound of formula I according to the process for synthesizing Micafungin in WO2004014879.

Crystal A of compound of formula I obtained in Example 2 of the present application (1.07 mmol, 1.00 g) was dissolved in 12 ml of DMF. The resulting solution was cooled to below 0° C. in an ice bath. Diisopropylethylamine (0.22 g, 1.67 mmol) was added, and the temperature was kept at 0° C. MKC-8 (1-[4-[5-(4-pentyloxyphenyl)isoxazol-3-yl]benzoyloxy]-1H-1,2,3-benzotriazole) (0.53 g, 1.14 mmol) was slowly added, and the reaction was warmed to 2-6° C., and maintained for 4 hours. 60 ml of ethyl acetate was added directly into the reaction liquid at the end of the reaction, stirred for another 1 hour, and filtered, so as to give micafungin diisopropylethylamine. The salt was dissolved in 30 ml of acetone and 30 ml of ethyl acetate, starching and filtered. Micafungin diisopropylethylamine was dried in vacuo to remove residual organic solvent. The purity of Micafungin diisopropylethylamine was determined as 99.15% by HPLC, and the yield was 91.6%.

Example 20

Preparation of the Compound of Formula II from Crystals B, C, D, E, F, G of Compound of Formula I The compound of formula II was synthesized from the compound of formula I according to the process for synthesizing Micafungin in WO2004014879.

Crystals B, C, D, E, F and G of compound of formula I obtained in Example 7, Example 14, Example 15, Example 16, Example 17 and Example 18 of the present application (1.07 mmol, 1.00 g) were dissolved in 12 ml of DMF, respectively. The resulting solution was cooled to below 0° C. in an ice bath. Diisopropylethylamine (0.22 g, 1.67 mmol) was added, and the temperature was kept at 0° C. MKC-8 (1-[4-[5-(4-pentyloxyphenyl)isoxazol-3-yl]benzoyloxy]-1H-1,2,3-benzotriazole) (0.53 g, 1.14 mmol) was slowly added, and the reaction was warmed to 2-6° C., and maintained for 4 hours. 60 ml of ethyl acetate was added directly into each reaction liquid at the end of the reaction, stirred for another 1 hour, and filtered, so as to give micafungin diisopropylethylamine. The salt was dissolved in 30 ml of acetone and 30 ml of ethyl acetate, starching and filtered. Micafungin diisopropylethylamine was dried in vacuo to remove residual organic solvent. The purity of Micafungin diisopropylethylamine was determined by HPLC.

Results and yield are shown in Table 1.

TABLE 1

| | Crystal | | | | | |
| --- | --- | --- | --- | --- | --- | --- |
| | B | C | D | E | F | G |
| HPLC purity % | 99.22% | 99.34% | 99.15% | 99.42% | 99.02% | 99.18% |
| yield % | 97.2% | 93.1% | 94.5% | 98.0% | 91.0% | 96.5% |

Comparative Example 1

Preparation of the Compound of Formula II from the Amorphous Solid of Compound of Formula I The compound of formula II was synthesized from the compound of formula I according to the process for synthesizing Micafungin in WO2004014879.

The amorphous powder of compound of formula I obtained in Example 1 of the present application (1.07 mmol, 1.00 g) was dissolved in 12 ml of DMF. The resulting solution was cooled to below 0° C. in an ice bath. Diisopropylethylamine (0.22 g, 1.67 mmol) was added, and the temperature was kept at 0° C. MKC-8 (1-[4-[5-(4-pentyloxyphenyl)isoxazol-3-yl]benzoyloxy]-1H-1,2,3-benzotriazole) (0.53 g, 1.14 mmol) was slowly added, and the reaction was warmed to 2-6° C., and maintained for 4 hours. 60 ml of ethyl acetate was added directly into the reaction liquid at the end of the reaction, stirred for another 1 hour, and filtered, so as to give micafungin diisopropylethylamine. The salt was dissolved in 30 ml of acetone and 30 ml of ethyl acetate, starching and filtered. Micafungin diisopropylethylamine was dried in vacuo to remove residual organic solvent. The purity of Micafungin diisopropylethylamine was determined as 95.75% by HPLC, and the yield was 75.2%.

From the above comparative example, it is clear that, compared with the amorphous solid of compound of formula I, HPLC purity and yield of the compound of formula II are significantly improved by using the compound of formula I with good crystal form.

Comparative Example 2

Effects of pH on the Preparation of the Crystal of Compound of Formula I

At 30° C., 1.2 g of the compound I prepared in Example 1 was dissolved into 6 ml of water by stirring. pH was adjusted to 1.8 using glacial acetic acid. 20 ml of ethanol was slowly added, and solids of compound I precipitated. The system was stirred for another 1 hour. 1.0 g of solid of compound of formula I was obtained by filtration, and dried in vacuo. The microstructure of solid was observed under a microscope and found that it was irregular solid, and XRPD pattern thereof can be found in FIG. 14.

Comparative Example 3

Effects of pH on the Preparation of the Crystal of Compound of Formula I

At 30° C., 1.2 g of the compound I prepared in Example 1 was dissolved into 6 ml of water by stirring. pH was adjusted to 5.4 using glacial acetic acid. 20 ml of ethanol was slowly added, and solids of compound I precipitated. The system was stirred for another 1 hour. 0.90 g of solid of compound of formula I was obtained by filtration, and dried in vacuo. The microstructure of solid was observed under a microscope and found that it was irregular solid, and XRPD pattern thereof can be found in FIG. 14.

Comparative Example 4

Effects of pH on the Preparation of the Crystal of Compound of Formula I

At 30° C., 1.2 g of the compound I prepared in Example 1 was dissolved into 6 ml of water by stirring. pH was adjusted to 6.5 using glacial acetic acid. 20 ml of ethanol was slowly added, and solids of compound I precipitated. The system was stirred for another 1 hour. 0.86 g of solid of compound of formula I was obtained by filtration, and dried in vacuo. The microstructure of solid was observed under a microscope and found that it was irregular solid, and XRPD pattern thereof can be found in FIG. 14.

Comparative Example 5

Effects of Solvents on the Preparation of the Crystal of Compound of Formula I

At 20° C., 2.4 g of the compound I prepared in Example 1 was dissolved into 7 ml of water. pH was adjusted to 4.0 using glacial acetic acid. The resulting mixture was stirred to completely dissolve compound I. 15 ml of acetonitrile was slowly added, the resulting mixture was stirred for 2 hours and solids precipitated. The microstructure of solide was observed under a microscope and found that it was irregular solid, and XRPD pattern thereof can be found in FIG. 14.

Comparative Example 6

Effects of Solvents on the Preparation of the Crystal of Compound of Formula I

At 8° C., 2.1 g of the compound I prepared in Example 1 was dissolved into 7 ml of water. pH was adjusted to 3.8 using glacial acetic acid. The resulting mixture was stirred to completely dissolve compound I. 20 ml of acetone was slowly added, the resulting mixture was stirred for 2 hours and solids precipitated. The microstructure of solid was observed under a microscope and found that it was irregular solid. The obtained compound of formula I was filtrated and vacuum-dried, and XRPD pattern thereof can be found in FIG. 14.

Comparative Example 7

Effects of the Concentration of Solution on the Preparation of the Crystal of Compound of Formula I At 10° C., 1.0 g of the solid powder of compound I prepared in Example 1 was dissolved into 25 ml. The resulting mixture was stirred to completely dissolve compound I. pH was adjusted to 4.5 using glacial acetic acid. 150 ml of n-propanol was slowly added, the resulting solution was cooled to −5° C. and stirred at −5° C. for 2 hours. 0.41 g of crystal A of compound of formula I was obtained by filtration, and dried in vacuo. The yield during the purification process was low primarily due to the low concentration of solution comprising the compound of formula I. Another 150 ml n-propanol was further added, and the resulting system was stirred at −5° C. for 2 hours. Only 0.52 g of crystal A of compound of formula I was obtained by filtration and vacuum drying. Therefore, the solution of compound I, the concentration of which is less than 50 mg/ml, is not suitable for the crystallization process and industrial production.

From the above comparative example, it is clear that the selection of pH during purification process is very important for obtaining the compound of formula I. If pH is not controlled within 2.0-5.0, it is difficult to obtain good crystals of the compound of formula I, the obtained solid was observed as amorphous solid under a microscope, and there is no characteristic peak for a crystal in XRPD pattern.

The selection of solvent is also very important for obtaining the compound of formula I. Except for the above solvents, good crystals of the compound of formula I can not be obtained by using other solvents. The obtained solid was observed as amorphous solid under a microscope, and there is no characteristic peak for a crystal in XRPD pattern.

Example 21

Purity and Stability Test

In this example, the purity and stability of the samples obtained in Comparative Examples and Examples were compared. The specific method is described as follows:

Samples from Comparative Example 2, Comparative Example 3, Comparative Example 4, Comparative Example 5, Comparative Example 6, Comparative Example 7, Example 1, Example 2, Example 3, Example 4, Example 5, Example 6, Example 7, Example 8, Example 9, Example 10, Example 11, Example 12, Example 13, Example 14, Example 15, Example 16, Example 17, Example 18 were obtained and placed into sealed containers at 0-8° C. for 7 days, respectively. And then the content of impurities in each sample was analyzed.

The results are shown in the following table 2.

| | Test conditions | |
| --- | --- | --- |
| Sample | Content of impurities in the initial sample | 0-8° C., content of impurities in the sample at 7 day |
| Comparative Example 2 | 1.9% | 3.4% |
| Comparative Example 3 | 1.9% | 3.2% |
| Comparative Example 4 | 1.8% | 2.9% |
| Comparative Example 5 | 2.1% | 3.6% |
| Comparative Example 6 | 2.4% | 4.1% |
| Comparative Example 7 | 2.4% | 4.7% |
| Example 1 | 2.5% | 4.8% |
| Example 2 | 0.5% | 0.5% |
| Example 3 | 0.5% | 0.5% |
| Example 4 | 0.5% | 0.7% |
| Example 5 | 0.4% | 0.4% |
| Example 6 | 0.5% | 0.5% |
| Example 7 | 0.4% | 0.5% |
| Example 8 | 0.5% | 0.5% |
| Example 9 | 0.5% | 0.6% |
| Example 10 | 0.4% | 0.4% |
| Example 11 | 0.4% | 0.5% |
| Example 12 | 0.3% | 0.4% |
| Example 13 | 0.3% | 0.4% |
| Example 14 | 0.4% | 0.5% |
| Example 15 | 0.3% | 0.4% |
| Example 16 | 0.3% | 0.4% |
| Example 17 | 0.3% | 0.4% |
| Example 18 | 0.4% | 0.5% |

From the above data, it can be seen that the crystals of compounds of formula I exhibit higher purity, and better stability after stored for a long period of time.

Example 22

Preparation of a Pharmaceutical Composition

| Crystal of compound of formula I | Lactose | Anhydrous citric acid | NaOH |
| --- | --- | --- | --- |
| 2.5 g | 20 g | q.s. | q.s. |

20 g of lactose was dissolved into pure water (200 ml) at the temperature lower than 50° C. After cooling below 20° C., into the lactose solution was added 2.5 g of crystal B of the compound of formula I obtained in Example 7. The resulting solution was gently stirred to avoid bubbles. 2% aqueous citric acid (0.95 ml) was added, and then into the solution was added 0.4% aqueous NaOH (approximately 24 ml) for adjusting pH to 5.5. And then the resulting solution was diluted with pure water to produce a given volume (250 ml). The resulting solution was filled into 100 vials (the volume of which is 10 ml) with 2.5 ml for each. The solution in each vial was lyophilized using the lyophilizer according to conventional methods, so as to obtain lyophilized compositions, with each containing 25 mg of crystal of compound I.

The above examples are merely the preferred examples for the present invention, and such examples cannot be used to limit the scope of the invention. The substantial technical contents according to the present invention are broadly defined in the claims. And any entities or methods accomplished by others should be considered as the equivalents and fall within the scope as defined by the claims, if said entities or methods are the same as those defined by the claims.

The invention claimed is:

1. A cyclopeptide comprising one or more compounds selected from the group consisting of:

crystal A of cyclopeptide of formula I, wherein R represents H or a cation capable of forming a pharmaceutically acceptable salt, and X-ray powder diffraction pattern (XRPD) of said crystal A shows characteristic peaks at the following 2θ angles: 7.1±0.2, 8.0±0.2, 14.7±0.2, 16.8±0.2, 18.9±0.2, 20.3±0.2, 21.1±0.2;

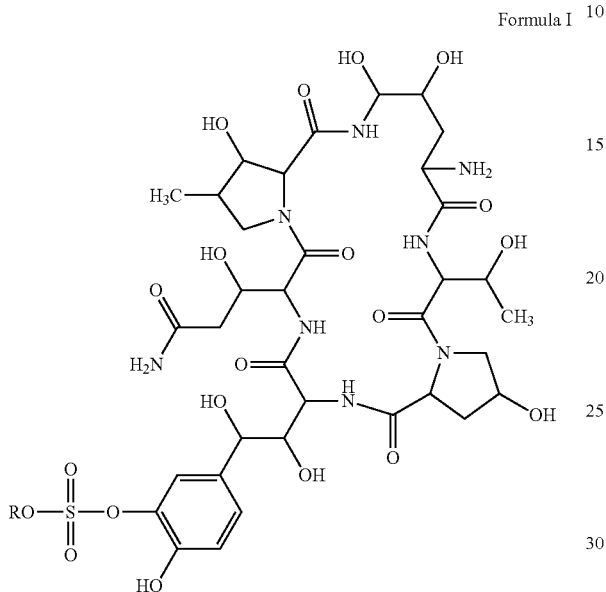

Formula I crystal B of cyclopeptide of formula I, wherein R represents H or a cation capable of forming a pharmaceutically acceptable salt, and X-ray powder diffraction pattern (XRPD) of said crystal B shows characteristic peaks at the following 2θ angles: 7.3±0.2°, 11.9±0.2°, 12.8±0.2°, 16.8±0.2°, 19.6±0.2°, 21.1±0.2°, 22.1±0.2°, 22.8±0.2°, 24.3±0.2°, 25.4±0.2°;

crystal C of cyclopeptide of formula I, wherein R represents H or a cation capable of forming a pharmaceutically acceptable salt, and X-ray powder diffraction pattern (XRPD) of said crystal C shows characteristic peaks at the following 2θ angles: 8.6±0.2°, 11.9±0.2°;

crystal D of cyclopeptide of formula I, wherein R represents H or a cation capable of forming a pharmaceutically acceptable salt, and X-ray powder diffraction pattern (XRPD) of said crystal D shows characteristic peaks at the following 2θ angles: 5.6±0.2°, 14.4±0.2°, 19.8±0.2°, 22.7±0.2°, 23.0±0.2°, 23.9±0.2°;

crystal E of cyclopeptide of formula I, wherein R represents H or a cation capable of forming a pharmaceutically acceptable salt, and X-ray powder diffraction pattern (XRPD) of said crystal E shows characteristic peaks at the following 2θ angles: 9.7±0.2°, 19.8±0.2°, 23.0±0.2°;

crystal F of cyclopeptide of formula I, wherein R represents H or a cation capable of forming a pharmaceutically acceptable salt, and X-ray powder diffraction pattern (XRPD) of said crystal F shows characteristic peaks at the following 2θ angles: 7.0±0.2°, 7.9±0.2°, 12.6±0.2°, 14.1±0.2°, 18.5±0.2°, 20.6±0.2°, 21.6±0.2°, 35.6±0.2°;

crystal G of cyclopeptide of formula I, wherein R represents H or a cation capable of forming a pharmaceutically acceptable salt, and X-ray powder diffraction pattern (XRPD) of said crystal G shows characteristic peaks at the following 2θ angles: 7.3±0.2°, 19.8±0.2°, 21.1±0.2°.

2. The cyclopeptide of claim 1, wherein X-ray powder diffraction pattern (XRPD) of said crystal A further shows characteristic peaks at the following 2θ angles: 7.3±0.2, 11.9±0.2, 12.3±0.2, 16.1±0.2, 18.5±0.2, 19.6±0.2, 22.1±0.2, 22.8±0.2, 23.1±0.2, 24.3±0.2, 25.4±0.2, 28.3±0.2, 33.5±0.2.

3. The cyclopeptide of claim 1, wherein X-ray powder diffraction pattern (XRPD) of said crystal D further shows characteristic peaks at the following 2θ angles: 7.4±0.2°, 8.2±0.2°, 9.7±0.2°, 12.2±0.2°, 16.5±0.2°, 18.6±0.2°, 22.3±0.2°, 28.2±0.2°.

4. The cyclopeptide of claim 1, comprising crystal F, wherein X-ray powder diffraction pattern (XRPD) of said crystal F further shows characteristic peaks at the following 2θ angles: 7.3±0.2°, 12.1±0.2°, 14.4±0.2°, 16.7±0.2°, 19.8±0.2°, 21.1±0.2°, 22.9±0.2°, 23.6±0.2°, 24.9±0.2°, 30.7±0.2°.

5. A cyclopeptide of Formula II, wherein R represents H or a cation capable of forming a pharmaceutically acceptable salt:

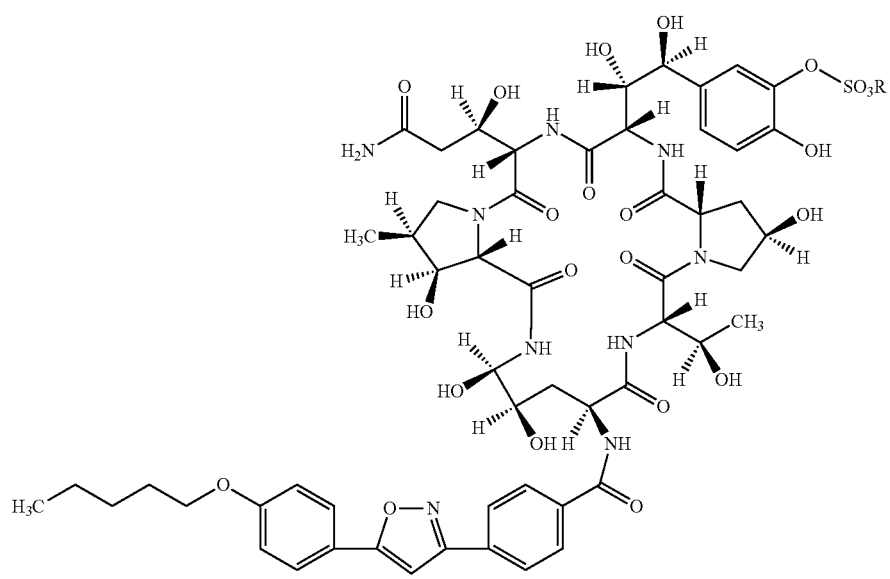

II wherein said cyclopepitde of Formula II is prepared from a crystal of the cyclopeptide according to claim 1.

6. A pharmaceutical composition comprising the crystal of the cyclopeptide of claim 1 and a pharmaceutically acceptable carrier.

7. A cyclopeptide composition comprising one or more compounds selected from the group consisting of the following: crystal A of the cyclopeptide, crystal B of the cyclopeptide, crystal C of the cyclopeptide.

8. A cyclopeptide composition comprising crystal D of the cyclopeptide and crystal E of the cyclopeptide.

9. A cyclopeptide composition comprising crystal F of the cyclopeptide and crystal G of the cyclopeptide.

* * * * *